(12) United States Patent
Han et al.

(10) Patent No.: US 10,407,402 B1
(45) Date of Patent: Sep. 10, 2019

(54) METHOD FOR SYNTHESIS OF CHALCOGENOPHENES

(71) Applicant: National Tsing Hua University, Hsinchu (TW)

(72) Inventors: Chien-Chung Han, Hsinchu (TW); Vamsi Krishna Karapala, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 16/275,278

(22) Filed: Feb. 13, 2019

(51) Int. Cl.
*C07D 345/00* (2006.01)
*C07D 421/04* (2006.01)
*C07F 7/08* (2006.01)

(52) U.S. Cl.
CPC ......... *C07D 345/00* (2013.01); *C07D 421/04* (2013.01); *C07F 7/0827* (2013.01)

(58) Field of Classification Search
CPC ............................ C07D 345/00; C07D 421/04
See application file for complete search history.

(56) References Cited

U.S. PATENT DOCUMENTS 3,542,764 A  11/1970  Mack

FOREIGN PATENT DOCUMENTS

GB   1107698   3/1968

OTHER PUBLICATIONS

Aymen Skhiri et al., "Unprecedented Access to b-Arylated Selenophenes through Palladium-Catalysed Direct Arylation", Chem. Eur. J., Feb. 2017, pp. 2788-2791.
Daniel P. Sweat et al., "Synthesis and Stille Cross-Coupling Reactions of 2-(Tributylstannyl)- and 2,5-Bis (trimethylstannyl)tellurophene", Synthesis, Aug. 2009, pp. 3214-3218.
Gang He et al., "Coaxing Solid-State Phosphorescence from Tellurophenes", Angew. Chem. Int. Ed., Mar. 2014, pp. 4587-4591.
Miguel J. Dabdoub et al., "Iodocyclization of (Z)-1-(Butyltelluro)-1,4-diorganylbut-1-en-3-ynes. Synthesis and Reactions of 3-Iodotellurophenes", J. Org. Chem., Jul. 1996, pp. 9503-9511.
Jean-Marie Catel et al., "Synthese Directe De Methyl-3 Et De Dimethyl-2,4 Selenophenes Et Tellurophenes", Phosphorus and Sulfur and the Related Elements, Dec. 2006, pp. 1-5.
Ashlee A. Jahnke et al., "Poly(3-alkyltellurophene)s Are Solution-Processable Polyheterocycles", J. Am. Chem. Soc., Jan. 2013, pp. 951-954.
Cristiano R. B. Rhoden et al., "New development of synthesis and reactivity of seleno- and tellurophenes", Org. Biomol. Chem., Nov. 2010, pp. 1301-1313.
Vamsi Krishna Karapala et al., "Cascade and Effective Syntheses of Functionalized Tellurophenes", Org. Lett., Mar. 2018, pp. 1550-1554.

*Primary Examiner* — Timothy R Rozof
(74) *Attorney, Agent, or Firm* — JCIPRNET

(57) ABSTRACT

A method of forming a chalcogenophene compound of formula (I) includes reacting a compound of formula (II) with a chalcogenide salt in presence of a proton source.

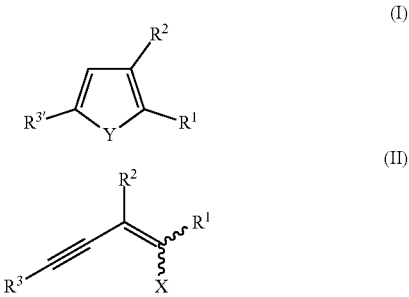

Y is O, S, Se, Te or Po. $R^1$ is hydrogen, deuterium, an aliphatic, heteroaromatic, or aromatic group, or a precursor of a leaving group Z whose conjugate acid (HZ) has $pK_a$ less than 30. $R^2$ is hydrogen, deuterium, or an aliphatic, heteroaromatic, or aromatic group. $R^1$ and $R^2$ may be the same or different, and may joint together to form a saturated or unsaturated, heteroalicyclic or alicyclic ring. $R^3$ is, for example, alkyl, aryl, heteroaryl, organosilyl, organotin, or organogermyl. $R^{3'}$ is the same as $R^3$ or is hydrogen. X is a precursor of a leaving group X whose conjugate acid (HX) has a $pK_a$ of less than 30.

20 Claims, No Drawings

METHOD FOR SYNTHESIS OF CHALCOGENOPHENES

BACKGROUND OF THE INVENTION

Field of Invention

This invention relates to functionalized chalcogenophenes and their preparation, and, more particularly, relates to a method and a composition for forming functionalized chalcogenophenes.

Description of Related Art

During the past few decades, functionalized chalcogenophenes have attracted significant research interest in both industrial and academic communities, because of their great application potentials and their novel electronic, optical, electrooptical, and opto-electronic properties. When compared to thiophenes, selenophenes and tellurophenes show desirable properties such as an enhanced stabilization of the LUMO energy levels, resulting in reduced optical band gap, increased polarizability, enhanced π-π interactions, and improved charge carrier mobility.

Although the properties of heavier chalcogenophenes seem desirable for the scientific community, the currently available synthetic routes towards functionalized chalcogenophenes are rare and often rather complex with unsatisfactorily low yields. For example, Skhiri et al. (*Chem. Eur J.*, 2017, 23(12), 2788-2791) reported the 3-arylation of selenophenes via metal-catalyzed cross coupling in presence of base and heating. In the reported protocol, selenophenes plus expensive and reactive arylsulfonyl chlorides have to be used as starting materials, and the method is limited to commercially available selenophenes to form only arylated compounds. Furthermore, no examples for heavier chalcogenophenes such as tellurophenes are reported.

Concerning tellurophenes, U.S. Pat. No. 3,542,764 discloses a preparation method involving reacting a metal telluride with substituted or unsubstituted 1,3-diynes. Other reported synthetic routes towards tellurophenes involve, for example, metal-catalyzed cross-coupling reactions with 2- and/or 5-substituted tellurophenes (Sweat and Stephens, *Synthesis*, 2009, 19, 3214-3218).

All these methods are suitable to prepare unsubstituted, 2- and/or 5-functionalized chalcogenophenes, whilst a reliable synthetic route towards 3-functionalized chalcogenophenes remains scarce. 3-Functionalized chalcogenophenes would be highly desirable as starting materials for the preparation of functional conjugated polymers, which are particularly interested for their applicability in the material sciences due to their highly conductive properties.

Although it could be expected that cross-coupling reactions of 3-halo-chalcogenophenes could yield the desired 3-functionalized derivatives, the preparation of the starting materials can be rather laborious, involving multistep syntheses and complex intermediates. For example, He et al. (*Angew. Chem. Int. Ed.*, 2014, 53, 4587-4591) reported the preparation of 3-bromo-tellurophenes through a complicated and multistep procedure via a series of novel intermediates such as 2,3,4,5-tetrakis(pinacolboronate)zirconacyclopentadiene, 2,3,4,5-tetrakis(pinacolboronate)tellurophene, and then 3-(pinacolboronate)tellurophene. Similarly, Dabdoub et al. (*J. Org. Chem.*, 1996, 61, 9503-9511) reported the preparation of 3-iodotellurophenes starting from 1,3-butadiyne and dibutyl ditelluride via iodine promoted cyclization of (Z)-tellurobutenynes intermediate. Catel et al. (*Phosphorus Sulfur Relat. Elem.*, 1987, 34, 119-121) and Jahnke et al. (*J. Am. Chem. Soc.*, 2013, 135, 951-954) have prepared 3-alkyltellurophenes by reacting telluride salts with a complicated, disubstituted propargylic alcohol, which is made by reacting an organomagnesium bromide with an expensive Weinreb amide. The reported yields are rather low (<35%). Other preparation methods for selenophenes and tellurophenes were recently reviewed by Rhoden and Zeni (*Org. Biomol. Chem.*, 2011, 9, 1301-1313).

All the methods mentioned above encounter at least one of the disadvantages of being limited to the production of 2- and/or 5-functionalized chalcogenophenes, requiring numerous reaction steps, using expensive materials, or resulting in low overall yields. Hence, there is a great need for an effective and easy synthesis of functionalized chalcogenophenes.

SUMMARY OF THE INVENTION

Accordingly, this disclosure provides an effective, low-cost method to prepare 3-functionalized, 2-functionalized, 2,5-functionalized, 2,3-functionalized, 2,4-functionalized, and 2,3,5-functionalized chalcogenophenes.

This disclosure also provides a reaction mixture to prepare 3-functionalized, 2-functionalized, 2,5-functionalized, 2,3-functionalized, 2,4-functionalized, and 2,3,5-functionalized chalcogenophenes.

This disclosure is based on the discovery of the high reactivity of 1-en-3-ynes compounds, further substituted in the 1-position with a suitable leaving group, with chalcogenides salts to directly yield 3-functionalized, 2-functionalized, 2,5-functionalized, 2,3-functionalized, 2,4-functionalized, and 2,3,5-functionalized chalcogenophene compounds.

In some embodiments of the present disclosure, a method of forming chalcogenophene compounds of formula (I) comprises reacting an enyne compound of formula (II) with a chalcogenide salt in the presence of a proton source.

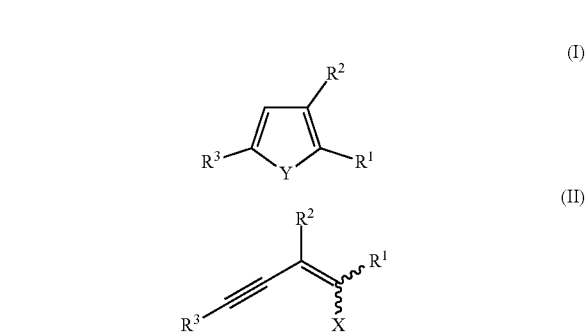

In formula (I) Y is either Po, Te, Se, S, or O. In formula (I) and in formula (II), $R^1$ is hydrogen, a deuterium, a substituted or unsubstituted aliphatic, heteroaromatic, or aromatic group, or a precursor of a good leaving group $Z^-$ whose conjugate acid has a $pK_a$ of less than 30. $R^2$ is a hydrogen, a deuterium, or a substituted or unsubstituted aliphatic, heteroaromatic, or aromatic group. $R^1$ and $R^2$ may be the same or different, and may joint together to form a substituted or unsubstituted, saturated or unsaturated, heteroalicyclic or alicyclic ring. $R^3$ is selected from the group consisting of hydrogen, deuterium, substituted and unsubstituted alkyl, aryl, heteroaryl, alkanoyl, aryloyl, heteroaryloyl, organosilyl (e.g., trialkylsilyl), organotin (e.g., trialkyltin), organogermyl (e.g., trialkylgermyl) groups. $R^{3'}$ is the same as R³ or hydrogen. In formula (II), X is a precursor of a good leaving group X⁻ whose conjugate acid has a $pK_a$ of less than 30.

In some embodiments of the present disclosure, in the compound of formula (II) R¹ and X are independently one of a halogen atom, a mesylate group, a triflate group, a tosylate group, an alkanesulfonate group, or an arenesulfonate group. In some embodiments, in formula (II) R¹ is the same as X.

In some embodiments of the present disclosure, it is possible that compounds of formula (II) in which R¹ is a hydrogen atom are generated in situ starting from a compound of formula (III)

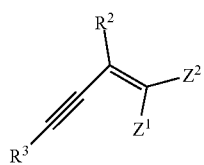

(III)

In formula (III), R² is hydrogen, deuterium, or a substituent. R³ is selected from the group consisting of hydrogen, deuterium, substituted and unsubstituted alkyl, aryl, heteroaryl, alkanoyl, aryloyl, heteroaryl, organosilyl (e.g., trialkylsilyl), organotin (e.g., trialkyltin), organogermyl (e.g., trialkylgermyl) groups. Each of Z¹ and Z² is independently a precursor of a leaving group $Z^{1-}$ or $Z^{2-}$ whose conjugate acid HZ¹ or HZ² has a $pK_a$ of less than 30.

In some embodiments, in the compound of formula (II) the precursor of a leaving group Z⁻ or X⁻ whose conjugate acid (HZ or HX) has a $pK_a$ of less than 30 is one of a halogen atom, a mesylate group, a triflate group, a tosylate group, an alkanesulfonate group, or an arenesulfonate group. In some embodiments, in the compound of formula (III) the precursor of a leaving group $Z^{1-}$ or $Z^{2-}$ whose conjugate acid HZ¹ or HZ² has a $pK_a$ of less than 30 is one of a halogen atom, a mesylate group, a triflate group, a tosylate group, an alkanesulfonate group, or an arenesulfonate group.

Without being bound by or limited to any chemical theory, it is possible that in the early stages of the reaction, compounds of formula (III) lose one of Z¹ and Z² to generate compounds of formula (II). It will be apparent to those skilled in the art that which one of Z¹ and Z² is lost from the compound of formula (III) to generate the compound of formula (II) in which R¹ is hydrogen or deuterium will be determined in each case by nature of Z¹ and Z² and the specific reaction conditions used.

Furthermore, in some alternative embodiments, a compound according to formula (II) may be generated in situ from other precursors than a compound of formula (III), or be prepared according to reported synthetic methods and directly reacted with a chalcogenide salt.

Without being bound by or limited to any chemical theory, it is possible that in the early stages of the reaction, a hydrochalcogenation of the compound of formula (II) occurs, leading to the formation of a compound of formula (IV).

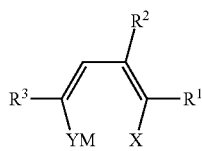

(IV)

In formula (IV), Y is either O, S, Te or Se, and M is a proton or a cation species. Subsequent deprotonation (when M is H), formation of a five-membered ring, and loss of the X group (not necessarily in this order) would then lead to the chalcogenophene compounds of formula (I).

In some embodiments of the present disclosure, compounds of formula (II) and compounds of formula (V) are observed together with compounds of formula (I).

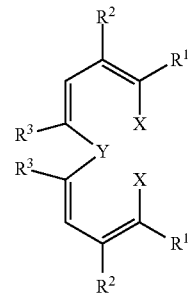

(V)

In some embodiments of the present disclosure, the chalcogenide salt can be prepared in situ, by reaction of elemental O, S, Se or Te. In some embodiments, elemental S, Se or Te are reacted with a reducing agent such as NaBH₄ in a nitrogen or argon atmosphere, but the disclosure is not limited thereto, and other preparation protocols of the chalcogenide salt might be followed, provided that they are compatible with the components of the reaction mixture. Depending on the chosen starting material, a compound of formula (II) is subsequently added to the chalcogenide salt.

In some embodiments of the present disclosure, the reaction between a compound according to formula (II) and the chalcogenide salt is carried out in a solvent. The inventors found out that polar solvents might promote the reaction, possibly because of a polarizing effect exercised on the covalent Y—H bonds of the chalcogenide salt or of some reaction intermediate. As such, in some embodiments of the present disclosure, the reaction is performed preferably in a solvent having a dielectric constant of at least 7, more preferably at least 15, and most preferably at least 30.

In some embodiments of the present disclosure, the reaction is performed at ambient temperature. The inventors found that for suitable substitutions patterns of compounds of formula (II) or formula (III) (for example, with compounds bearing aryl or heteroaryl substituents), the reaction can proceed smoothly without need to provide extra energy in the form of heat. Without being bound to or limited by any chemical theory, it is possible that some substituents stabilize charges or partial charges that build up during the course of the reaction, hence lowering the activation energies required for the corresponding elementary steps and allowing the reaction to proceed without heating the reaction mixture. In some embodiments, compounds of formula (II) or formula (III) may not benefit from the aforementioned stabilization effect (for example, in the case of alkyl substituted compounds), and heating may be required for the reaction to proceed. In some alternative embodiments, the reaction may be performed with heating even if the substitution pattern would provide the stabilization effect, for example to shorten the reaction time.

In some embodiments of the present disclosure, when $R^3$ in compounds of formula (II) is an organosilyl group, such as trialkylsilyl, desilylation might occur during the reaction, so that in the isolated compound of formula (I), $R^3$ ends up being a hydrogen atom. In some embodiments, desilylation might be promoted by addition of base or by heating the reaction mixture at an elevated temperature, such as at 50° C.

In some embodiments of the present disclosure, a base can be added to the reaction mixture to facilitate the ring closure reaction. The basicity of the used base can vary widely, depending on the nature of the substituents present on the compound of formula (II) or (III) and the employed reaction conditions, such as the solvent medium and the reaction temperature. In general, when the reaction is performed in a relative polar solvent medium or at a higher temperature, a relatively weak base can be used. In some cases, for example when reaction of a compound of formula (II) or (III) having at least one aryl or an electron-deficient group (which can help stabilize the negative charge developed on the molecule during the cyclization) is performed in a highly polar solvent medium like N,N-dimethylformamide (DMF), DMF itself (whose conjugated acid has a $pK_a$ of −1.2) can work as an effective base to accept the proton that is released during the ring-formation step. In some other cases, a stronger base, such as NaOH or KOH can be used to facilitate the reaction. In some embodiments, the $pK_a$ of the conjugated acid of the base is preferably less than 50, more preferably less than 40, and most preferably less than 30. When a weaker base is used, the reaction can tolerate a broader range of substituent groups.

In some embodiments of the present disclosure, one or more additives may be added to the reaction mixture. Different additives may play different roles in promoting the reaction. In some embodiments, the $pK_a$ of a first additive is preferably less than 40, more preferably less than 30, and most preferably less than 20.

Without being bound to or limited by any chemical theory, the first additive may act as a proton source to enhance the solubility of the chalcogenide salts, or to protonate reaction intermediates.

In some embodiments, a second additive may be a co-solvent having a dielectric constant of at least 7, more preferably at least 15, and most preferably at least 30. The second additive may raise the polarity of the reaction medium, increasing the polarization of bonds that have to be heterolytically cleaved for the reaction to proceed, or may enhance the nucleophilic character of chalcogenol species that act as nucleophiles during the reaction courses.

In some embodiments of the present disclosure, a mixture to prepare chalcogenophenes compounds according to formula (I) is provided. In some embodiments, the mixture includes a compound according to formula (II) and a chalcogenide salt. In some alternative embodiments, the mixture includes a compound according to formula (II) and a source of a chalcogenide salt. In some embodiments, the source of the chalcogenide salt may include elemental S, Se or Te. In some embodiments, the compound of formula (II) may be mixed with the chalcogenide salt. In some embodiments, the chalcogenide salt may be generated in situ by suitable precursors, and the compound of formula (II) may be added to the chalcogenide salt.

The present disclosure provides methods and compositions allowing preparation of 3-functionalized, 2-functionalized, 2,5-functionalized, 2,3-functionalized, 2,4-functionalized, and 2,3,5-functionalized chalcogenophene compounds in moderate to high yields. In some embodiments, reactions according to the present disclosure may be carried out under mild conditions, for example without heating or without addition of base reagent. The reaction can tolerate the presence of various functional groups in the starting materials, including halogenated compounds, heteroaromatic rings, or the like. Even sterically hindered substrates can successfully yield the desired chalcogenophenes.

In order to make the aforementioned and other objects, features, and advantages of this invention comprehensible, several embodiments are described in detail below.

It should be noted that although mechanistic hypothesis concerning the path followed by the reaction are presented, such discussions are provided in the attempt to rationalize the role of the individual components included in the method and the effects observed on the reaction outcome, but they are not to be construed as limitations of the present disclosure. In other words, the disclosure is not intended to be bound to or limited by any chemical theory, nor by any reaction mechanism suggested or discussed herein.

Within the present disclosure, the expression "ambient temperature" identifies the temperature of the surrounding atmosphere of the reactor, which was about 25° C.

DESCRIPTION OF EMBODIMENTS

It is first noted that the term "a compound of formula (I)" is sometimes called "a compound (I)" hereafter for simplicity. The same rule applies to formulae (II), (III), (IV), and (V), and specific examples thereof.

The group $R^3$ in the above formulae (II)—(V) is selected from the group consisting of hydrogen, deuterium, substituted and unsubstituted alkyl, aryl, heteroaryl, alkanoyl, aryloyl, heteroaryl, organosilyl (e.g., trialkylsilyl), organotin (e.g., trialkyltin), organogermyl (e.g., trialkylgermyl) groups. In formula (I), $R^{3'}$ may be the same as $R^3$ in formula (II) or be hydrogen. The group Y in the above formulae (I), (IV) and (V) is either O, S, Te or Se.

The groups $Z^1$ and $Z^2$ in the above formulae (II)—(V) are independently a precursor of a leaving group $Z^{1-}$ or $Z^{2-}$ whose conjugate acid ($HZ^1$ or $HZ^2$) has a $pK_a$ of less than 30. In some embodiments, the groups $Z^1$ and $Z^2$ are independently one of a halogen atom, a mesylate group, a triflate group, a tosylate group, an alkanesulfonate group, or an arenesulfonate group.

<Substituents $R^1$ and $R^2$ in Formulae (I)-(V)>

$R^1$ in formulae (I), (II), (IV), and (V) is selected from the group consisting of hydrogen, deuterium, a substituted or unsubstituted aliphatic, heteroaromatic, or aromatic group, or a precursor of a leaving group $Z^-$ whose conjugate acid (HZ) has a $pK_a$ of less than 30. In some embodiments, $R^1$ is one of a halogen atom, a mesylate group, a triflate group, a tosylate group, an alkanesulfonate group, or an arenesulfonate group.

$R^2$ is hydrogen, deuterium, or a substituted or unsubstituted aliphatic, heteroaromatic, or aromatic group. $R^1$ and $R^2$ group may be selected independently from each other.

The substituted or unsubstituted aliphatic, heteroaromatic, or aromatic groups to be used as $R^1$ or $R^2$ in formulae (I)-(V) is independently selected from the group consisting of hydrogen, deuterium, alkyl, alkenyl, alkynyl, alkenynyl, aryl, alkylaryl, arylalkyl, allyl, benzyl, alkoxy, aryloxy, cycloalkyl, cycloalkenyl, cycloalkynyl, cycloalkenynyl, alkanoyl, aryloyl, aryloyloxy, alkanoyloxy, alkylthio, arylthio, alkylthioalkyl, alkylthioaryl, arylthioaryl, mercaptoalkoxy, mercaptoaryloxy, mercaptoalkyl, mercaptoaryl, mercaptoarylthio, mercaptoalkylthio, mercaptoalkylarylalkyl, mercaptoarylalkylaryl, halo, hydroxyl, hydroxyalkyl, hydroxyaryl, cyano, nitro, alkylsilyl, arylsilyl, alkoxysilyl, aryloxysilyl, mercapto, epoxy moieties, alkoxyalkyl, aryloxyalkyl, alkoxycarbonyl, alkoxysilylalkyl, alkylsilylalkyl, alkoxysilylaryl, alkylsilylaryl, heterocyclic ring, heteroaromatic ring, alkylsulfinyl, arylsulfinyl, alkylsulfonyl, arylsulfonyl, alkylsulfinylalkyl, alkylsulfonylalkyl, alkylcarboxylate, alkylsulfinate, alkylsulfonate, alkylphosphonate; derivatives of various acid functional groups including phosphonic acid, phosphinic acid, boric acid, carboxylic acid, sulfinic acid, sulfonic acid, sulfamic acid, and amino acid, wherein the acid derivatives may include ester, amide and metal salt; aliphatic moieties having a repeating unit of —(OCH$_2$CH$_2$)$_q$OCH$_3$, —(OCH$_2$CH(CH$_3$))$_q$OCH$_3$, —(CH$_2$)$_q$CF$_3$, —(CF$_2$)$_q$CF$_3$ or —(CH$_2$)$_q$CH$_3$, wherein q≥1; and a moiety of (OR$^4$)$_r$OR$^5$, wherein R$^4$ is a divalent C$_{1-7}$ alkylene moiety, R$^5$ is C$_{1-20}$ alkyl, 1≤r≤50. All the abovementioned substituent groups may be further substituted with allowable functional groups, such as ester, amino acid, halo, epoxy, amino, silyl, nitro, alkoxy, aryloxy, and arylthio groups.

Further, R$^1$ and R$^2$ may be the same substituent or different substituents, and may joint together to form a substituted or unsubstituted alkylene, alkenylene, or alkynylene chain completing a heteroalicyclic or alicyclic ring system, which may include one or more heteroatoms and/or divalent moieties such as nitrogen, sulfur, sulfinyl, sulfonyl, phosphorus, selenium, ester, carbonyl, and oxygen, wherein permissible substituents are the substituted or unsubstituted aliphatic, heteroaromatic, or aromatic groups listed.

The aromatic or heteroaromatic group to be used as R$^1$, R$^2$, R$^3$ or as the aromatic or heteroaromatic substituent appearing on the ring formed when R$^1$ and R$^2$ joint is selected from the group consisting of substituted and unsubstituted, mono- and poly-nuclear, aryl and heteroaryl moieties. The aryl or heteroaryl moieties preferably denote a mono-, bi- or tricyclic aromatic or heteroaromatic group with up to 40 carbon atoms that may also comprise condensed rings and is optionally substituted. Preferred aryl groups include, without limitation, benzene, biphenylene, triphenylene, naphthalene, anthracene, binaphthylene, phenanthrene, pyrene, dihydropyrene, chrysene, perylene, tetracene, pentacene, benzpyrene, fluorene, indene, indenofluorene, spirobifluorene, and the like. Preferred heteroaryl groups include, without limitation, 5-membered rings like pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 6-membered rings like pyridine, pyridazine, pyrimidine, pyrazine, 1,3,5-triazine, 1,2,4-triazine, 1,2,3-triazine, 1,2,4,5-tetrazine, 1,2,3,4-tetrazine, 1,2,3,5-tetrazine, and fused systems like carbazole, indole, isoindole, indolizine, indazole, benzimidazole, benzotriazole, purine, naphthimidazole, phenanthrimidazole, pyridimidazole, pyrazinimidazole, quinoxalinimidazole, benzoxazole, naphthoxazole, anthroxazole, phenanthroxazole, isoxazole, benzothiazole, benzofuran, isobenzofuran, dibenzofuran, quinoline, isoquinoline, pteridine, benzo-5,6-quinoline, benzo-6,7-quinoline, benzo-7,8-quinoline, benzoisoquinoline, acridine, phenothiazine, phenoxazine, benzopyridazine, benzopyrimidine, quinoxaline, phenazine, naphthyridine, azacarbazole, benzocarboline, phenanthridine, phenanthroline, thieno[2,3b]thiophene, thieno[3,2b]thiophene, dithienothiophene, dithienopyridine, isobenzothiophene, dibenzothiophene, benzothiadiazothiophene, or combinations thereof. The heteroaryl groups may be substituted with allowable functional groups, such as acid, ester, amino acid, halo, epoxy, amino, silyl, nitro, alkoxy, aryloxy, arylthio, alkyl, fluoro, fluoroalkyl, or further aryl or heteroaryl substituents.

<Chalcogenide Salts>

Chalcogenide salts serve, amongst other functions, as the source of the chalcogenide atom included in the chalcogenophene compound of formula (I). The term "chalcogen" refers to atoms of Group VIB of the Periodic Table of Elements, such as O, S, Se, Te, and Po. The term "chalcogenide salt" refers to a binary or multinary compound containing at least one chalcogen and at least one cationic group or cationic element from the periodic table. In some embodiments, the cationic groups or cationic elements used are from alkali, alkaline earth, transition, and main group elements. In some embodiments, possible chalcogenide salts used are "A$_1$A$_2$A$_3$ . . . A$_x$Y$_n$", where "A$_1$, A$_2$, A$_3$, . . . A$_x$" are different cationic groups and/or elements and "Y$_n$" is a chalcogen, such as in salts like Li$_2$Y, Na$_2$Y, Na$_2$Y$_2$, K$_2$Y, Rb$_2$Y, Cs$_2$Y, BeY, MgY, CaY, SrY, BaY or hydrogenated versions thereof. In some preferred embodiments, Na$_2$Y or a Na$_2$Y/NaHY mixture is used as chalcogenide salt. In some embodiments, the chalcogenide salt is prepared in situ starting from elemental chalcogen in presence of a reducing agent. In some embodiments, the cation of the chalcogenide salt is produced from the reducing agent used. In some embodiments, the reducing agent is chosen from the group consisting of hydride delivering reducing agents such as sodium hydride, lithium hydride, calcium hydride, sodium borohydride, lithium triethylborohydride, and all other boron and aluminum hydrides. In some embodiments, the reducing agent is chosen from sulfur-oxygen salts such as sodium hydroxymethanesulfinate, sodium hydroxymethanesulfonate, sodium dithionite and so on. In some embodiments, the reducing agent is chosen from the group consisting of organic bases and organic salts such as ammonia, hydrazine hydrate, tosyl hydrazine, sodium naphthalenide and so on.

<Base>

In the embodiments where a base is added to the reaction mixture, any base can be used provided that it is chemically compatible with the substituents on the compounds of formulae (II) and (III) or the protected version thereof. The pK$_a$ of the conjugated acid of the base is preferably less than 50, and more preferably less than 40, and most preferably less than 30. In some embodiments, the use of a weaker base is preferred, so that the reaction can tolerate a broader range of substituent groups. In some embodiments when the dielectric constant of either the solvent, the co-solvent, or the additive is less than ~26, the base is preferably a strong base having a conjugate acid with a pK$_a$ in the range from 5 to 50, such as hydroxide ion, carbonate ion, hydrogen carbonate ion, and hydride ion. In some embodiments, the conjugate acid of the base may act as the proton source. In some embodiments, when amphoteric compounds (e.g., hydrogen carbonate salts) are used as the base, the base itself may also act as a proton source. In some embodiments when the dielectric constant of either the solvent, the co-solvent, or the additive is greater than ~26, the useful base can be a weak base, such as an alcohol, a ketone, an ether, a nitrile, N,N-dimethylformamide (DMF), N,N-dimethylacetamide (DMAc), dimethylsulfoxide (DMSO), N-methyl-2-pyrrolidone (NMP), and hexamethylphosphoramide (HMPA). In some embodiments, the weak base may also serve as a polar additive, a proton-source additive, or a co-solvent. In some embodiments, a combination of more than one types of bases can be used.

The base might be used to promote the ring-closure reaction by deprotonating from the intermediate chalcogenol species of formula (IV) (when M in formula (IV) is a proton) before the ring closure step, or from the transition state or intermediate species during or after the ring closure reaction.
<Solvents>

The components of the reaction mixture used to implement this invention can be either in a neat liquid form, a pure solid form, or a molten form, or as a solute form dissolved or dispersed in a given solvent medium. For example, a compound of formula (II) or (III) may be added as a neat liquid or as a solution to the chalcogenide salt. In some embodiments, the chalcogenide salt may also be a solution or a suspension. The resultant mixture may form a single miscible liquid phase at the first moment, or it may form initially a biphasic system that may then gradually turn into a monophasic mixture or remain a biphasic system as the reaction proceeds with time.

Any solvent or solvent mixture can be used as the desirable solvent medium in implementing the present invention as long as it can help dissolve, disperse, mix, or bring into contact the compound of formula (II) or formula (III) with the chalcogenide salt. Illustrative of useful solvents include alcohols, linear and cyclic ethers, hydrocarbons, halogen-containing hydrocarbons, aromatics, ketones, amides, nitriles, carbonate esters, HMPA, sulfoxides and other sulfur containing solvents, nitro substituted alkanes and aromatics, water or mixtures thereof.

Exemplary alcohols include methanol, ethanol, isopropanol, and the like. Illustrative linear and cyclic ethers include tetrahydrofuran, tetrahydropyran, 2-methyltetrahydrofuran, diethyl ether, diglyme, glyme, dipropyl ether, diisopropyl ether, dibutyl ether, methyl butyl ether, diphenyl ether, dioxane, diethylene glycol, ethylene glycol (EG), and the like. Illustrative aliphatic hydrocarbons include hexane, heptane, octane, nonane, decane, cyclopentane, cyclohexane, and the like. Exemplary halogen-containing hydrocarbons, include dichloromethane, chloroform, 1,2-dichloroethane, carbon tetrachloride, dichloroethane, dibromoethane, trichloroethane, tribromoethane, tetrachloroethane, and the like. Illustrative aromatics include xylene, anisole, toluene, benzene, cumene, mesitylene, phenol, cresol, dichlorobenzene, chlorobenzene, and the like. Exemplary ketones include acetone, propanone, butanone, pentanone, hexanone, heptanone, octanone, acetophenone, and the like. Illustrative amides include N,N-dimethylformamide, N,N-dimethylacetamide, N-methylacetamide, acetamide, N-methyl-2-pyrrolidinone, pyrrolidinone, and the like. Exemplary nitriles include acetonitrile, propionitrile, benzonitrile, butyronitrile, and the like. Illustrative sulfoxides and other sulfur containing solvents include dimethylsulfoxide, and the like. Illustrative nitro substituted alkanes and aromatics include nitromethane, nitroethane, nitropropane, nitroisopropane, nitrobenzene, and the like. Exemplary carbonate esters include propylene carbonate, ethylene carbonate, and the like. In general, the amount of solvent or solvent mixture employed to carry the reaction is not critical, so long as the reactive starting molecules and the chalcogenide salt can be dissolved or dispersed, mixed or contacted with each other. In some embodiments, the solvent may act as a proton source.

In some embodiments, a solvent with a dielectric constant of at least 7, more preferably at least 15, and most preferably at least 30 is used. Without being bound to nor limited by any chemical theory, it is possible that solvents of higher polarity might promote deprotonation of the chalcogenol of formula (IV) or of the hydrogenated chalcogenide salt by increasing the polarization of the Y—H bond, leading to an increased negative charge on the chalcogen atom, with a consequent enhancement of the nucleophilic character of the chalcogen atom, and to an increased positive charge on the bonded proton, with a consequent enhancement of the acidic character of the bonded proton. The increased nucleophilicity of the chalcogen atom might promote the hydrochalcogenation reaction with the alkyne moiety in the compound of formula (II) to yield the chalcogenol of formula (IV) and the nucleophilic cyclization reaction to form the five-membered ring. The increased acidity of the chalcogenol proton in compound (IV) might promote the deprotonation reaction (aided or not by the base) before or during the cyclization step. In some preferred embodiments, an alcohol with up to 12 carbon atoms, or an amide with up to 10 carbon atoms is used as a solvent. In some more preferred embodiments, ethanol or N,N-dimethylformamide are used as a solvent.
<Additives>

In some embodiments, additives can be added to the reaction mixture to promote the reaction. In some embodiments, multiple additives may be used to perform different functions within the reaction mixtures. For example, additives may be used as proton sources when aprotic solvents are used as main solvent for the reaction, or to increase the polarity of the reaction medium. Without being bound by or limited to any chemical theory, a proton source might be required to form or solubilize the chalcogenide salts at the beginning of the reaction, whilst a more polar reaction environment might promote polarization of bonds within the reactants or the reaction intermediates.

In some embodiments, a first additive is added to the reaction to act as a proton source. The $pK_a$ of the first additive is preferably less than 40, more preferably less than 30, and even more preferably less than 20. In some embodiments, first additives include substituted and unsubstituted alcohols such as methanol, ethanol, trifluoroethanol, 1-propanol, isopropanol, hexafluoroisopropanol, 1-butanol, 2-butanol, tert-butanol, hexanol, phenol, and the like. In some preferred embodiments, alcohols up to 12 carbon atoms are used as first additive, and the volume ratio of the first additive to the solvent is in the range from 0.001 to 5.

In some embodiments, a second additive may be added to the reaction mixture. The second additive may have a dielectric constant of at least 7, more preferably at least 15, and even more preferably at least 30. Illustrative second additives are N,N-dimethylformamide, dimethylacetamide, N-methylacetamide, acetamide, N-methyl-2-pyrrolidinone, pyrrolidinone, dimethylsulfoxide, HMPA, THF, acetone, acetonitrile, methanol, ethanol, propanol, butanol, tert-butanol, and water. A ratio of the volume of solvent to the volume of second additive is not particularly limited, and may be determined also based on the solubility of the other components of the reaction mixture. In some embodiments, the ratio of the volume of solvent to the volume of the second additive may be in the range from 99:1 to 1:99. In some preferred embodiments, water is used as second additive.
<Reaction Temperature and Reaction Time>

The useful reaction temperatures to implement this invention can vary widely, depending on the nature of the starting reactants and their substitution pattern. Since this invention provides a very effective method for making chalcogenophenes, most of the reactions can undergo efficiently to give moderate to high yields within rather short time intervals (such as between 1 hour up to 3 hours) at ambient temperature or under moderate heating temperatures (e.g., up to 75° C.). In some cases, when performing the reaction at ambient temperature, prolonging the reaction time (up to 48 hours) might be desirable to reach higher conversion of the starting material. If a silylated compound (II) or a silylated compound (III) is used as a staring material, and retention of the silyl group is desired in the chalcogenophene compound (I), performing the reaction at ambient temperature, with shorter reaction times (about 1 h) and without adding base might be preferable, provided that the chosen starting compound of formula (II) or formula (III) is reactive under the selected conditions. Aryl- or heteroaryl-functionalized compounds are particularly suitable to react at ambient temperature, while alkyl-functionalized compounds tend to require a somewhat more energic heating (up to 140° C., or, in some embodiments, up to 200° C.). If so desired, more energic heating (e.g., from about 50° C. up to 200° C.) can be applied to aryl- or heteroaryl-functionalized starting materials, resulting in shortening of the reaction times (all the way down to about 30 minutes) without significant changes in the isolated yield of compound (I). From the economical point of view, it might be desirable to perform the reaction at ambient temperature, which is a convenient and energy saving approach.

<Different Embodiments for the Formation of Chalcogenophene Compounds>

In some embodiments of the method of forming chalcogenophene compounds of formula (I), the method comprises reacting a compound according to formula (II) with a chalcogenide salt in presence of a proton source.

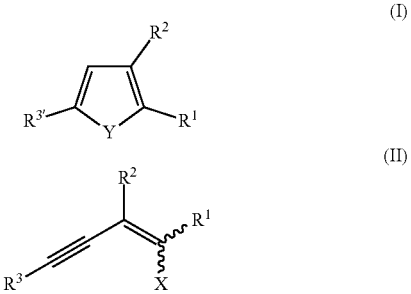

In formula (I), Y is either O, S, Te, Se or Po. In formula (I) and in formula (II) $R^1$ is hydrogen, deuterium, a substituted or unsubstituted aliphatic, heteroaromatic, or aromatic group, or a precursor of a leaving group Z whose conjugate acid (HZ) has a $pK_a$ of less than 30. $R^2$ is hydrogen, deuterium, or a substituted or unsubstituted aliphatic, heteroaromatic, or aromatic group. $R^1$ and $R^2$ may be the same or different, and may joint together to form a ring. $R^3$ is selected from the group consisting of hydrogen, deuterium, substituted and unsubstituted alkyl, aryl, heteroaryl, alkanoyl and aryloyl, heteroaryl, organosilyl (e.g., trialkylsilyl), organotin (e.g., trialkyltin), organogermyl (e.g., trialkylgermyl) groups. $R^{3'}$ may be the same as $R^3$ or hydrogen. In formula (II), X is a precursor of a leaving group X whose conjugate acid (HX) has a $pK_a$ of less than 30. In some embodiments, the precursor of the leaving group Z or X whose conjugate acid (HZ or HX) has a $pK_a$ of less than 30 is one of a halogen atom, a mesylate group, a triflate group, a tosylate group, an alkanesulfonate group, or an arenesulfonate group.

In some embodiments of the present disclosure, in the compound of formula (II) $R^1$ and X are independently one of a halogen atom, a mesylate group, a triflate group, a tosylate group, an alkanesulfonate group, or an arenesulfonate group. In some embodiments, in formula (II) $R^1$ is the same as X.

In some embodiments in which $R^1$ is a hydrogen atom, the compound of formula (II) is generated in situ from a compound of formula (III).

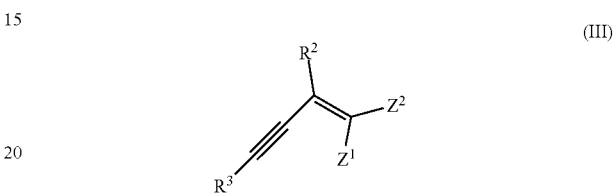

In formula (III), $R^2$ is hydrogen, deuterium, or a substituent. $R^3$ is selected from the group consisting of hydrogen, deuterium, substituted and unsubstituted alkyl, aryl, heteroaryl, alkanoyl and aryloyl, heteroaryl, organosilyl (e.g., trialkylsilyl), organotin (e.g., trialkyltin), organogermyl (e.g., trialkylgermyl) groups. Each of $Z^1$ and $Z^2$ is independently a precursor of a leaving group $Z^{1-}$ or $Z^{2-}$ whose conjugate acid ($HZ^1$ or $HZ^2$) has a $pK_a$ of less than 30. In some embodiments, the precursor of the leaving group $Z^{1-}$ or $Z^{2-}$ whose conjugate acid ($HZ^1$ or $HZ^2$) has a $pK_a$ of less than 30 is one of a halogen atom, a mesylate group, a triflate group, a tosylate group, an alkanesulfonate group, or an arenesulfonate group.

In some embodiments, a compound of formula (II) or a compound of formula (III) is mixed with the chalcogenide salt.

In another embodiment, the reaction is carried in a solvent having a dielectric constant of at least 7. In some embodiments, the reaction is stirred at ambient temperature. In some embodiments, $R^2$ is a substituted or unsubstituted aromatic or heteroaromatic group. It is possible that the solvent is an aprotic solvent, a first additive is added to the reaction, and a $pK_a$ of the first additive is less than 40. In some embodiments, the $pK_a$ of the first additive is preferably less than 40, and more preferably less than 30, and most preferably less than 20. It is possible that the ratio of the volume of the first additive to the volume of solvent is in the range from 0.001 to 5. It is possible that the first additive is a $C_1$ to $C_{12}$ alcohol. In some embodiments, the solvent is the proton source.

In another embodiment, a second additive having a dielectric constant higher than the dielectric constant of the solvent is added to the reaction, and a ratio of the volume of solvent over the volume of second additive is in the range from 99:1 to 1:99. It is possible that a $C_1$ to-$C_{12}$ alcohol is used as a solvent, and water is used as a second additive.

In another embodiment, a base is added to the reaction, and the $pK_a$ of a conjugate acid of the base is preferably less than 50, more preferably less than 40, and most preferably less than 30.

In some embodiments, wherein, when the dielectric constant of the solvent or the additive is less than 26, the base is selected from the group whose conjugate acid has a $pK_a$ in the range from 5 to 50. It is possible that the base, its conjugated acid, or both are the proton source. It is possible that an amphoteric compound is used as the base.

In some embodiments, when the dielectric constant of the solvent or the additive is greater than 26, the base is selected from the group consisting of an alcohol, a ketone, an ether, a nitrile, N,N-dimethylformamide, N,N-dimethylacetamide, dimethylsulfoxide, N-methyl-2-pyrrolidone, and hexamethylphosphoramide.

In some embodiments, $R^3$ is selected from the group consisting of substituted and unsubstituted organosilyl, organotin, and organogermyl groups.

In some embodiments, the reaction system is heated at a temperature between 50° C. and 200° C.

<Potential Applications>

The chalcogenophene compounds of formula (I) prepared according to the present invention can be used for any purpose. For example, they can be attached to bioactive molecules and be used as molecular probes or reporter. In this regard, tellurophene-containing isotopologous probes can be used as potential mass tags, biomarkers, and barcoding reagents for the analysis of cells using mass cytometry to measure the intensity of affected tumor cells. Selenophene derived compounds can be used as antiprotozoal agents. Selenophene based novel conducting polymers, such as poly(2-(2-octyldodecyl)-4,7-di-(selenoph-2-yl)-2H-enzo[d][1,2,3]triazole) (PSBTz), can be used to enhance the biosensor performance in the detection of cholesterol and glucose. Selenophene based ribonucleoside analogs, which have a (selenophen-2-yl)pyrimidine core, can be used as fluorescence probes to study the function of RNA in real time. Fluorescently labeled selenophene-containing ARC type inhibitors (adenosine analogues and arginine-rich peptides), ARC-Lum probes, can induce long life time photoluminescence when attached to proteins (e.g., protein kinases (PK)). These probes can be used for determination of activity of basophilic PKs, characterization of inhibitors of PKs, and as sensors for bioactive molecules (e.g., cAMP). Selenophene analogues of piperidinyl quinoline antibacterial agents can display improved activity against the primary target enzyme DNA gyrase (type IIA bacterial topoisomerase) compared to the thiophene analogue.

The chalcogenophene compounds can also be polymerised to form conjugated homo- or co-polymers, used for many potential applications. Conjugated polymers comprising repeat units of chalcogenophenes may be used, like other conjugated conducting polymers, in the fabrication of articles that comprise electrically conductive portions and electrically non-conductive portions, and articles that are completely electrically conductive. Examples of useful applications include productions of coatings to form electrically conductive polymer housings for EMI shielding of sensitive electronic equipment such as microprocessors; infrared, radio frequency and microwave absorbing shields; flexible electrical conducting connectors; conductive bearings and brushes; semiconducting photoconductor junctions; electrodes; capacitors; field effect transistors; organic memory devices; solar cell device; photovoltaic cells; super capacitor; sensors; smart cards; nonlinear optical materials; medical applications; artificial muscle; reinforcement materials and/or additives; optically transparent or non-transparent corrosion-preventing coatings for corrodible materials such as steel; antistatic materials and optically transparent or non-transparent coatings for packaging electronic components; antistatic carpet fibers; antistatic waxes for floors in computer rooms; antistatic finishes for CRT screens, aircraft, and auto windows, and the like.

The following examples are presented to more particularly illustrate the present invention, and should not be construed as being limitations on the scope and spirit of the present invention.

EXAMPLES

The following examples are intended to further explain the current disclosure, but are not to be construed as limiting the scope of the present invention.

In the following examples, the groups $R^1$, $R^2$, $R^3$, Y, X, $Z^1$, and $Z^2$ are identified and referred to as indicated below: C5 indicates an n-pentyl group, C7 indicates an n-heptyl group, TMS indicates a trimethylsilyl group, Ph indicates a phenyl group, hydrogen, tellurium and selenium are indicated by the respective chemical symbols (H, Te, Se). Other substituents are identified and referred to with the abbreviations reported in Table 1. In Table 1, * indicates a bonding site of the substituent group.

TABLE 1

Abbreviations for indicating some substituent groups used in the examples

| Abbreviation | Structure | |
|---|---|---|
| Cl—Ph | Z=Cl | |
| Br—Ph | Z=Br | |
| CF₃—Ph | Z=CF₃ | *—⟨phenyl⟩—Z |
| Me—Ph | Z=Me | |
| OMe—Ph | Z=OMe | |
| NAP | 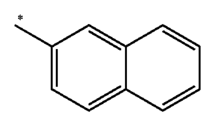 | *—⟨naphthyl⟩ |
| FUR | 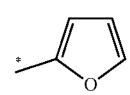 | *—⟨furanyl⟩ |
| TP | 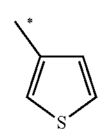 | *—⟨thiophenyl⟩ |

<General Information>

NMR spectra were obtained on Bruker 400 MHz, 600 MHz and Varian 400 MHz spectrometers. Chemical shifts are reported in parts per million ((ppm) referenced to CDCl₃ ((7.24 for $^1$H NMR and (77.00 for $^{13}$C NMR), CFCl₃ ((0.00 for $^{19}$F NMR), Ph₂Te₂ in CDCl₃ ((422 for $^{125}$Te NMR) and selenophene in CDCl₃ ((605 for $^{77}$Se NMR). Multiplicities are indicated by s (singlet), d (doublet), t (triplet), q (quartet), p (pentet), dd (doublet of doublets), dt (doublet of triplets), and m (multiplet). Coupling constants J are reported in Hertz (Hz). High-resolution mass spectra (HRMS) were obtained with JEOL JMS-T200GC, AccuTOF GCx (HR field ionization (FI)/HR field desorption (FD)) spectrometers.

Example 1A: Preparation of (3-(dibromomethylene)oct-1-yn-1-yl)trimethylsilane (II-1)

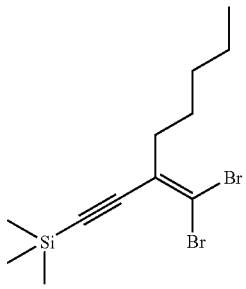

(II-1)

Ethynyltrimethylsilane (0.01 mol, 1.0 equiv) was dissolved in dry tetrahydrofuran (20 mL) and the reaction mixture was cooled to 0° C. n-BuLi (2.5 M in hexanes, 0.011 mol, 1.1 equiv) was added dropwise to the solution. The reaction mixture was stirred for 30 min at ambient temperature. After cooling to 0° C., hexanal (0.01 mol, 1.0 equiv) was slowly added to the solution. The reaction mixture was allowed to warm to ambient temperature and stirred for additional 2 hours. The reaction was quenched with a saturated aqueous solution of ammonium chloride and was extracted three times with ethyl acetate (50 mL each). The combined organic phases were dried over magnesium sulfate and filtered. The solvent was removed under reduced pressure. The obtained propargylic alcohol (0.01 mol, 1.0 equiv) was slowly added to a suspension of pyridinium dichromate (0.011 mol, 1.1 equiv) and 4 Å molecular sieves (100% weight equivalent to the propargylic alcohol) in dry dichloromethane (50 mL) under dry conditions. After complete conversion of the starting material (as determined by TLC) the suspension was filtered through a celite bed, the filtrate was collected, and the solvent was evaporated under reduced pressure. The crude product was purified by column chromatography (eluent: n-hexane). To the obtained ynone (0.004 mol, 1.0 equiv) in dry dichloromethane (50 mL) were sequentially added triphenylphosphine (0.012 mol, 3.0 equiv) and tetrabromomethane (0.006 mol, 1.5 equiv) at ambient temperature. The reaction mixture was allowed to stir at ambient temperature until complete conversion (as detected by TLC). The suspension was diluted with n-hexane (150 mL) and filtered over a short column of silica (eluent: n-hexane: ethyl acetate, 9:1, vol:vol). The solvent was removed under reduced pressure to obtain quantitatively pure compound (II-1) as a pale yellow liquid.

$^{1}$H NMR (400 MHz, CDCl$_3$): δ 2.29 (t, J=7.6 Hz, 2H), 1.59-1.51 (m, 2H), 1.36-1.23 (m, 4H), 0.88 (t, J=6.8 Hz, 3H), 0.19 (s, 9H). $^{13}$C NMR (100 MHz, CDCl$_3$): δ 131.1, 103.1, 102.7, 97.5, 36.7, 31.0, 27.1, 22.4, 13.9, −0.3. HRMS-FI: Calculated 349.9696, Found 349.9704, Δ=2.47 ppm.

Examples 1B-1V: Preparation of Compounds of Formula (II)

The compounds of formulae (II-2) to (II-22) indicated in table 2 below were obtained following the same protocol as indicated for compound (II-1) in Example 1A, by using the appropriate aldehydes and alkyne compounds as starting material. In all cases, the compounds were obtained in quantitative yield.

TABLE 2

Compounds of formula (II) prepared in Examples 1A to 1W

| Entry | Compound of formula (II) | R$^2$ | R$^3$ | R$^1$ | X |
|---|---|---|---|---|---|
| Example 1A | II-1 | C5 | TMS | Br | Br |
| Example 1B | II-2 | C7 | TMS | Br | Br |
| Example 1C | II-3 | C7 | Ph | Br | Br |
| Example 1D | II-4 | Ph | TMS | Br | Br |
| Example 1E | II-5 | Ph | Ph | Br | Br |
| Example 1F | II-6 | Ph | H | Br | Br |
| Example 1G | II-7 | Ph | tBu | Br | Br |
| Example 1H | II-8 | Ph | MePh | Br | Br |
| Example 1I | II-9 | Cl—Ph | TMS | Br | Br |
| Example 1J | II-10 | Cl—Ph | Ph | Br | Br |
| Example 1K | II-11 | CF$_3$—Ph | TMS | Br | Br |
| Example 1L | II-12 | CF$_3$—Ph | Ph | Br | Br |
| Example 1M | II-13 | Me—Ph | TMS | Br | Br |
| Example 1N | II-14 | Me—Ph | Ph | Br | Br |
| Example 1O | II-15 | OMe—Ph | TMS | Br | Br |
| Example 1P | II-16 | OMe—Ph | Ph | Br | Br |
| Example 1Q | II-17 | FUR | TMS | Br | Br |
| Example 1R | II-18 | TP | TMS | Br | Br |
| Example 1S | II-19 | Br—Ph | Ph | Br | Br |
| Example 1T | II-20 | NAP | TMS | Br | Br |
| Example 1U | II-21 | NAP | Ph | Br | Br |
| Example 1V | II-22 | NAP | H | Br | Br |

Example 1B: Preparation of (3-(dibromomethylene)dec-1-yn-1-yl)trimethylsilane (II-2)

Isolated as a pale yellow liquid quantitatively. $^{1}$H NMR (400 MHz, CDCl$_3$): δ 2.29 (t, J=7.6 Hz, 2H), 1.58-1.50 (m, 2H), 1.29-1.24 (m, 8H), 0.87 (t, J=6.8 Hz, 3H), 0.19 (s, 9H). $^{13}$C NMR (100 MHz, CDCl$_3$): δ 131.1, 103.1, 102.7, 97.5, 36.7, 31.7, 29.0, 28.8, 27.4, 22.6, 14.1, −0.3. HRMS-FI: Calculated 378.0008, Found 378.0062, Δ=14.18 ppm.

Example 1C: Preparation of (3-(dibromomethylene)dec-1-yn-1-yl)benzene (II-3)

Isolated as a brown liquid quantitatively. $^{1}$H NMR (400 MHz, CDCl$_3$): δ 7.47-7.45 (m, 2H), 7.34-7.30 (m, 3H), 2.40 (t, J=7.6 Hz, 2H), 1.66-1.59 (m, 2H), 1.37-1.23 (m, 8H), 0.87 (t, J=6.9 Hz, 3H). $^{13}$C NMR (100 MHz, CDCl$_3$): δ 131.5, 131.1, 128.7, 128.4, 122.8, 96.8, 96.3, 88.0, 36.9, 31.7, 29.0, 28.9, 27.6, 22.6, 14.1. HRMS-FI: Calculated 381.9926, Found 381.9920, Δ=−2.23 ppm.

Example 1D: Preparation of (4,4-dibromo-3-phenylbut-3-en-1-yn-1-yl)trimethylsilane (II-4)

Isolated as a yellow liquid quantitatively. $^{1}$H NMR (400 MHz, CDCl$_3$): δ 7.43-7.40 (m, 2H), 7.38-7.33 (m, 3H), −0.19 (s, 9H). $^{13}$C NMR (100 MHz, CDCl$_3$): δ 137.8, 131.0, 128.6, 128.5, 128.3, 104.1, 103.3, 100.3, −0.4. HRMS-FI: Calculated 355.9226, Found 355.9230, Δ=1.25 ppm.

Example 1E: Preparation of (1,1-dibromo-4-phenylbut-1-en-3-yn-2-yl)benzene (II-5)

Isolated as a pale yellow liquid quantitatively. $^{1}$H NMR (400 MHz, CDCl$_3$): δ 7.51-7.46 (m, 4H), 7.42-7.28 (m, 6H). $^{13}$C NMR (100 MHz, CDCl$_3$): δ 138.0, 131.5, 131.0, 129.0 (2 peaks merged), 128.6 (2 peaks merged), 128.4, 122.5, 99.0, 97.6, 88.9. HRMS-FI: Calculated 359.9144, Found 359.9147, Δ=0.79 ppm.

Example 1F: Preparation of (1,1-dibromobut-1-en-3-yn-2-yl)benzene (II-6)

Isolated as a brown liquid quantitatively. $^1$H NMR (600 MHz, CDCl$_3$): δ 7.44-7.42 (m, 2H), 7.39-7.33 (m, 3H), 3.59 (s, 1H). $^{13}$C NMR (150 MHz, CDCl$_3$): δ 137.7, 128.7, 128.5, 128.4, 100.8, 85.8 (2 peaks merged), 82.7. HRMS-FI: Calculated 283.8831, Found 283.8840, Δ=3.52 ppm.

Example 1G: Preparation of (1,1-dibromo-5,5-dimethylhex-1-en-3-yn-2-yl)benzene (II-7)

Isolated as a light brown liquid quantitatively. $^1$H NMR (400 MHz, CDCl$_3$): δ 7.43-7.40 (m, 2H), 7.36-7.31 (m, 3H), 1.25 (s, 9H). $^{13}$C NMR (100 MHz, CDCl$_3$): δ 138.5, 131.2, 128.6, 128.3, 128.2, 107.6, 97.3, 79.4, 30.5, 28.5. HRMS-FI: Calculated 339.9457, Found 339.9449, Δ=−2.23 ppm.

Example 1H: Preparation of 1-(4,4-dibromo-3-phenylbut-3-en-1-yn-1-yl)-4-methylbenzene (II-8)

Isolated as a pale yellow solid quantitatively. $^1$H NMR (400 MHz, CDCl$_3$): δ 7.49-7.46 (m, 2H), 7.40-7.34 (m, 5H), 7.11 (d, J=8 Hz, 2H), 2.32 (s, 3H). $^{13}$C NMR (100 MHz, CDCl$_3$): δ 139.3, 138.1, 131.5, 131.1, 129.1, 128.6, 128.5, 128.4, 119.5, 98.5, 98.0, 88.4, 21.6. HRMS-FI: Calculated 373.9300, Found 373.9299, Δ=−0.13 ppm.

Example 1I: Preparation of (4,4-dibromo-3-(4-chlorophenyl)but-3-en-1-yn-1-yl)trimethylsilane (II-9)

Isolated as a pale yellow solid quantitatively. $^1$H NMR (400 MHz, CDCl$_3$): δ 7.34 (m, 4H), 0.19 (s, 9H). $^{13}$C NMR (100 MHz, CDCl$_3$): δ 136.2, 134.5, 130.0, 129.8, 128.6, 104.6, 102.9, 100.8, −0.4. HRMS-FI: Calculated 389.8836, Found 389.8848, Δ=3.03 ppm.

Example 1J: Preparation of 1-chloro-4-(1,1-dibromo-4-phenylbut-1-en-3-yn-2-yl)benzene (II-10)

Isolated as an off-white solid quantitatively. $^1$H NMR (400 MHz, CDCl$_3$): δ 7.46-7.41 (m, 4H), 7.37-7.28 (m, 5H). $^{13}$C NMR (100 MHz, CDCl$_3$): δ 136.4, 134.6, 131.5, 130.0, 129.8, 129.1, 128.7, 128.4, 122.3, 99.5, 97.9, 88.6. HRMS-FI: Calculated 393.8754, Found 393.8752, Δ=−0.53 ppm.

Example 1K: Preparation of (4,4-dibromo-3-(4-(trifluoromethyl)phenyl)but-3-en-1-yn-1-yl)trimethylsilane (II-11)

Isolated as a pale yellow solid quantitatively. $^1$H NMR (600 MHz, CDCl$_3$): δ 7.63 (d, J=8.5 Hz, 2H), 7.56 (d, J=8.5 Hz, 2H), 0.22 (s, 9H). $^{13}$C NMR (150 MHz, CDCl$_3$): δ 141.3, 130.5 (q, J=32.6 Hz), 129.8, 129.0, 125.4 (q, J=3.2 Hz), 123.9 (q, J=271.4 Hz), 105.1, 102.7, 101.6, −0.4. $^{19}$F NMR (563 MHz, CDCl$_3$): δ −62.7 (s, CF$_3$). HRMS-FI: Calculated 423.9100, Found 423.9101, Δ=0.35 ppm.

Example 1L: Preparation of 1-(1,1-dibromo-4-phenylbut-1-en-3-yn-2-yl)-4-(trifluoromethyl)benzene (II-12)

Isolated as a colorless liquid quantitatively. $^1$H NMR (400 MHz, CDCl$_3$): δ 7.67-7.59 (m, 3H), 7.47-7.44 (m, 2H), 7.35-7.28 (m, 4H). $^{13}$C NMR (100 MHz, CDCl$_3$): δ 141.5, 133.7 (q, J=19.3 Hz), 131.8 (q, J=19.3 Hz), 130.5 (q, J=32.5 Hz), 129.2, 129.1, 128.4, 125.4 (q, J=3.7 Hz), 123.9 (q, J=270.6 Hz), 122.1, 100.2, 98.2, 88.3. $^{19}$F NMR (376 MHz, CDCl$_3$): δ −62.7 (s, CF$_3$). HRMS-FI: Calculated 427.9018, Found 427.9014, Δ=−0.85 ppm.

Example 1M: Preparation of (4,4-dibromo-3-(p-tolyl)but-3-en-1-yn-1-yl)trimethylsilane (II-13)

Isolated as a colorless liquid quantitatively. $^1$H NMR (600 MHz, CDCl$_3$): δ 7.32 (d, J=8.2 Hz, 2H), 7.17 (d, J=8.2 Hz, 2H), 2.34 (s, 3H), 1.25 (n-hexane grease peak), 0.20 (s, 9H). $^{13}$C NMR (150 MHz, CDCl$_3$): δ 138.5, 134.9, 130.9, 129.0, 128.4, 103.9, 103.4, 99.8, 29.7 (n-hexane grease peak), 21.3, −0.4. HRMS-FI: Calculated 369.9382, Found 369.9380, Δ=−0.63 ppm.

Example 1N: Preparation of 1-(1,1-dibromo-4-phenylbut-1-en-3-yn-2-yl)-4-methylbenzene (II-14)

Isolated as a pale yellow liquid quantitatively. $^1$H NMR (400 MHz, CDCl$_3$): δ 7.47-7.44 (m, 2H), 7.39 (d, J=8.1 Hz, 2H), 7.35-7.27 (m, 3H), 7.20 (d, J=8.3 Hz, 2H), 2.36 (s, 3H). $^{13}$C NMR (100 MHz, CDCl$_3$): δ 138.6, 135.1, 131.5, 130.9, 129.1, 128.9, 128.5, 128.3, 122.6, 98.5, 97.4, 89.0, 21.4. HRMS-FI: Calculated 373.9300, Found 373.9309, Δ=2.45 ppm.

Example 1O: Preparation of (4,4-dibromo-3-(4-methoxyphenyl)but-3-en-1-yn-1-yl)trimethylsilane (II-15)

Isolated as a colorless liquid quantitatively. $^1$H NMR (400 MHz, CDCl$_3$): δ 7.39-7.35 (m, 2H), 6.89-6.85 (m, 2H), 3.80 (s, 3H), 0.19 (s, 9H). $^{13}$C NMR (100 MHz, CDCl$_3$): δ 159.6, 130.5, 130.0, 113.6, 103.8, 103.5, 99.3, 55.3, −0.4. HRMS-FI: Calculated 385.9332, Found 385.9330, Δ=−0.45 ppm.

Example 1P: Preparation of 1-(1,1-dibromo-4-phenylbut-1-en-3-yn-2-yl)-4-methoxybenzene (II-16)

Isolated as an off-white solid quantitatively. $^1$H NMR (400 MHz, CDCl$_3$): δ 7.48-7.42 (m, 4H), 7.33-7.28 (m, 3H), 6.92-6.88 (m, 2H), 3.82 (s, 3H). $^{13}$C NMR (100 MHz, CDCl$_3$): δ 159.6, 131.5, 130.5, 130.2, 130.0, 128.9, 128.4, 122.6, 113.7, 98.1, 97.3, 89.1, 55.3. HRMS-FI: Calculated 389.9249, Found 389.9239, Δ=−2.73 ppm.

Example 1Q: Preparation of (4,4-dibromo-3-(furan-2-yl)but-3-en-1-yn-1-yl)trimethylsilane (II-17)

Isolated as a brown liquid quantitatively. $^1$H NMR (400 MHz, CDCl$_3$): δ 7.47 (d, J=0.8 Hz, 1H), 6.86 (d, J=3.1 Hz, 1H), 6.43-6.42 (m, 1 h), 0.24 (s, 9H). $^{13}$C NMR (100 MHz, CDCl$_3$): δ 149.0, 142.9, 120.8, 113.1, 111.4, 103.3, 101.2, 97.3, −0.4. HRMS-FI: Calculated 345.9019, Found 345.9025, Δ=1.82 ppm.

Example 1R: Preparation of (4,4-dibromo-3-(thiophen-3-yl)but-3-en-1-yn-1-yl)trimethylsilane (II-18)

Isolated as a brown liquid quantitatively. $^1$H NMR (400 MHz, CDCl$_3$): δ 7.60 (dd, J=3.0 and 1.4 Hz, 1H), 7.35 (dd, J=5.1 and 1.3 Hz, 1H), 7.26 (dd, J=5.1 and 3.1 Hz, 1H), 0.21 (s, 9H). $^{13}$C NMR (100 MHz, CDCl$_3$): δ 136.8, 128.1, 126.1, 125.8, 124.8, 103.3, 99.1, −0.4. HRMS-FI: Calculated 361.8790, Found 361.8788, Δ=−0.50 ppm.

Example 1S: Preparation of 1-bromo-4-(1,1-dibromo-4-phenylbut-1-en-3-yn-2-yl)benzene (II-19)

Isolated as an off-white solid quantitatively. $^1$H NMR (400 MHz, CDCl$_3$): δ 7.53-7.50 (m, 2H), 7.47-7.44 (m, 2H), 7.40-7.28 (m, 5H). $^{13}$C NMR (100 MHz, CDCl$_3$): δ 136.9, 131.6, 131.5, 130.3, 129.9, 129.1, 128.4, 122.8, 122.3, 99.4, 97.9, 88.5. HRMS-FI: Calculated 437.8249, Found 437.8247, Δ=−0.32 ppm.

Example 1T: Preparation of (4,4-dibromo-3-(naphthalen-2-yl)but-3-en-1-yn-1-yl)trimethylsilane (II-20)

Isolated as a light brown solid quantitatively. $^1$H NMR (400 MHz, CDCl$_3$): δ 7.90 (s, 1H), 7.83 (t, J=7.8, 3H), 7.49 (m, 3H), 0.20 (s, 9H). $^{13}$C NMR (100 MHz, CDCl$_3$): δ 135.2, 133.0, 132.9, 131.0, 128.2, 128.1, 128.0, 127.7, 126.7, 126.4, 125.9, 104.4, 103.3, 100.5, −0.4. HRMS-FI: Calculated 405.9382, Found 405.9378, Δ=−1.13 ppm.

Example 1U: Preparation of 2-(1,1-dibromo-4-phenylbut-1-en-3-yn-2-yl)naphthalene (II-21)

Isolated as an off-white solid quantitatively. $^1$H NMR (400 MHz, CDCl$_3$): δ 7.97 (d, J=1.3 Hz, 1H), 7.87-7.83 (m, 3H), 7.58 (dd, J=8.6 and 1.7 Hz, 1H), 7.59-7.46 (m, 4H), 7.36-7.28 (m, 3H). $^{13}$C NMR (100 MHz, CDCl$_3$): δ 135.4, 133.0, 132.9, 131.6, 131.0, 129.0, 128.4, 128.3, 128.1, 128.0, 127.7, 126.8, 126.5, 126.0, 122.5, 99.2, 97.8, 89.0. HRMS-FI: Calculated 409.9300, Found 409.9296, Δ=−1.10 ppm.

Example 1V: Preparation of 2-(1,1-dibromobut-1-en-3-yn-2-yl)naphthalene (II-22)

Isolated as a light brown solid quantitatively. $^1$H NMR (600 MHz, CDCl$_3$): δ 7.92 (d, J=1.1 Hz, 1H), 7.85-7.82 (m, 3H), 7.53-7.49 (m, 3H), 3.63 (s, 1H). $^{13}$C NMR (150 MHz, CDCl$_3$): δ 135.0, 133.0, 132.9, 133.1, 128.2, 128.1 (2 peaks merged), 127.7, 126.9, 126.5, 125.7, 101.0, 86.0, 82.7. HRMS-FI: Calculated 333.8987, Found 333.8996, Δ=2.80 ppm.

Examples 2A-2P: Preparation of Functionalized Chalcogenophenes

<First Protocol P1 for the Preparation of Functionalized Chalcogenophenes>

Elemental chalcogen (3.0 mmol, 3.0 equiv) was suspended in a liquid system (20 mL) constituted by ethanol and water, using the ratio between the volume of solvent and the volume of additive reported in Table 3. The elemental chalcogen was treated with sodium borohydride (9.0 mmol, 9.0 equiv) under nitrogen in a 2-neck round bottom flask fitted with a condenser. The mixture was heated to reflux for 2.5 hours. The solution was subsequently cooled to 0° C. and a degassed solution of compound of formula (II) in the same solvent indicated in Table 3 (5.0 mL) was added slowly. The reaction was maintained at 0° C. for one hour before being warmed to ambient temperature. An ethanolic solution (4.0 mL) of the base indicated in Table 3 (2.0 mmol, 2.0 equiv) was added. Each reaction was stirred at 75° C. for the time indicated in Table 3. Each reaction was quenched by stirring vigorously while exposed to laboratory air, diluted with ethyl acetate (50 mL) and filtered through celite. The filtrate was washed twice with water (50 mL each) and once with brine (50 mL) and was dried over magnesium sulfate. After evaporation of the solvent, the residue was purified by silica gel chromatography (eluent system indicated in the characterization data of each compound) to afford a functionalized chalcogenophene compound of formula (I) in the yields reported in Table 3.

For all the Examples in Tables 3, tellurium was used as chalcogen (Y=Te in formula (I)).

TABLE 3

Preparation of chalcogenophene compounds according to the first protocol P1

| Entry | Product of formula (I) | Reactant of formula (II) | Solvent: Additive (v:v) | Base (equiv.[a]) | Time (h) | Yield[b] (%) |
|---|---|---|---|---|---|---|
| Example 2A | I-1 | II-1 | 9:1 | KOH (2.0) | 3 | 32 |
| Example 2B | I-1 | II-1 | 9:1 | KOH (2.0) | 3 | 63 |
| Example 2C | I-1 | II-1 | 8:2 | KOH (2.0) | 3 | 76 |
| Example 2D | I-1 | II-1 | 7:3 | KOH (2.0) | 3 | 62 |
| Example 2E | I-1 | II-1 | 8:2 | NaOH (2.0) | 3 | 69 |
| Example 2F | I-2 | II-2 | 8:2 | KOH (2.0) | 8 | 71 |
| Example 2G | I-3 | II-4 | 8:2 | KOH (2.0) | 3 | 96 |
| Example 2H | I-4 | II-9 | 8:2 | KOH (2.0) | 3 | 92 |
| Example 2I | I-5 | II-11 | 8:2 | KOH (2.0) | 3 | 96 |
| Example 2J | I-6 | II-13 | 8:2 | KOH (2.0) | 3 | 81 |
| Example 2K | I-6 | II-13 | 8:2 | KOH (2.0) | 8 | 89 |
| Example 2L | I-7 | II-15 | 8:2 | KOH (2.0) | 3 | 74 |
| Example 2M | I-7 | II-15 | 8:2 | KOH (2.0) | 8 | 82 |
| Example 2N | I-8 | II-17 | 8:2 | KOH (2.0) | 3 | 89 |
| Example 2O | I-9 | II-18 | 8:2 | KOH (2.0) | 3 | 83 |
| Example 2P | I-10 | II-20 | 8:2 | KOH (2.0) | 3 | 95 |

[a]equiv. vs. mol. of compound (II) used
[b]Isolated yield

Examples 2A-2E: Preparation of 3-n-pentyltellurophene (I-1)

The reaction was performed using 0.2 mmol of compound (II-1). Purification via column chromatography on silica gel (n-hexane) gave the chalcogenophene of formula (I-1) as a brown color liquid. $^1$H NMR (600 MHz, CDCl$_3$): δ 8.76 (dd, J=6.6 and 1.9 Hz, 1H), 8.32 (m, un-resolved dd, 1H), 7.74 (dd, J=6.6 and 1.4 Hz, 1H), 2.60 (t, J=7.6 Hz, 2H), 1.60 (p, J=7.6 Hz, 2H), 1.34-1.28 (m, 4H), 0.88 (t, J=7.0 Hz, 3H). $^{13}$C NMR (150 MHz, CDCl$_3$): (153.0, 140.1, 124.0, 117.8, 34.8, 31.5, 30.0, 22.5, 14.0. $^{125}$Te NMR (188 MHz, CDCl$_3$): δ 766.8. HRMS-FI: Calculated 252.0152, Found 252.0147, Δ=−2.19 ppm.

Example 2F: Preparation of 3-n-heptyltellurophene (I-2)

The reaction was performed using 0.2 mmol of compound (II-2). Purification via column chromatography on silica gel (n-hexane) gave the chalcogenophene of formula (I-2) as a light brown color liquid. $^1$H NMR (600 MHz, CDCl$_3$): δ 8.76 (dd, J=6.6 and 1.9 Hz, 1H), 8.31 (m, un-resolved dd, 1H), 7.74 (dd, J=6.6 and 1.4 Hz, 1H), 2.60 (t, J=7.6 Hz, 2H), 1.63-1.57 (m, 2H), 1.32-1.24 (m, 8H), 0.87 (t, J=6.8 Hz, 3H). $^{13}$C NMR (150 MHz, CDCl$_3$): δ 152.9, 140.0, 124.0, 117.8, 34.8, 31.8, 30.3, 29.3, 29.1, 22.6, 14.1. $^{125}$Te NMR (188 MHz, CDCl$_3$): δ 767.2. HRMS-FI: Calculated 280.0465, Found 280.0474, Δ=3.17 ppm.

Example 2G: Preparation of 3-phenyltellurophene (I-3)

The reaction was performed using 1 mmol of compound (II-3). Purified by silica gel chromatography (n-hexane)

gave the chalcogenophene of formula (I-3) as a pale yellow solid. $^1$H NMR (600 MHz, CDCl$_3$): δ 8.96-8.94 (m, 2H), 8.29 (dd, J=6.6 and 1.6 Hz, 1H), 7.63-7.61 (m, 2H), 7.43-7.40 (m, 2H), 7.35-7.32 (m, 1H). $^{13}$C NMR (150 MHz, CDCl$_3$): δ 152.1, 139.6, 138.2, 128.6, 130.0, 126.9, 125.3, 120.8. HRMS-FI: Calculated 257.9683, Found 257.9684, Δ=0.61 ppm.

Example 2H: Preparation of
3-(4-chlorophenyl)tellurophene (I-4)

The reaction was performed using 0.2 mmol of compound (II-9). Purification via column chromatography on silica gel (n-hexane) gave the chalcogenophene of formula (I-4) as a pale yellow solid. $^1$H NMR (600 MHz, CDCl$_3$): δ 8.95-8.92 (m, 2H), 8.20 (dd, J=6.6 and 1.6 Hz, 1H), 7.51-7.48 (m, 2H), 7.35-7.33 (m, 2H). $^{13}$C NMR (150 MHz, CDCl$_3$): δ 150.8, 138.0, 137.8, 132.8, 128.7, 128.1, 125.8, 121.3. HRMS-FI: Calculated 291.9293, Found 291.9283, Δ=−3.28 ppm.

Example 2I: Preparation of
3-(4-(trifluoromethyl)phenyl)tellurophene (I-5)

The reaction was performed using 0.2 mmol of compound (II-11). Purification via column chromatography on silica gel (n-hexane) gave the chalcogenophene of formula (I-5) as an off white solid. $^1$H NMR (600 MHz, CDCl$_3$): δ 9.05 (t, J=1.5 Hz, 1H), 8.98 (dd, J=6.7 and 1.8 Hz, 1H), 8.25 (dd, J=6.7 and 1.4 Hz, 1H), 7.67 (d, J=8.4 Hz, 2H), 7.63 (d, J=8.4 Hz, 2H), 1.25 (n-hexane grease peak), 0.87 (n-hexane grease peak). $^{13}$C NMR (150 MHz, CDCl$_3$): δ 150.7, 142.9, 137.7, 128.9 (q, J=32.3 Hz), 127.1, 126.5 (q, J=271.4 Hz), 126.3, 125.6 (q, J=3.6 Hz), 123.0, 29.7 (n-hexane grease peak). $^{19}$F NMR (563 MHz, CDCl$_3$): δ −62.1 (s, CF$_3$). HRMS-FI: Calculated 325.9556, Found 325.9552, Δ=−1.50 ppm.

Examples 2J-2K: Preparation of
3-(p-tolyl)tellurophene (I-6)

The reaction was performed using 0.2 mmol of compound (II-13). Purification via column chromatography on silica gel (n-hexane) gave the chalcogenophene of formula (I-6) as an off white solid. $^1$H NMR (600 MHz, CDCl$_3$): δ 8.92 (dd, J=6.7 Hz and 1.9 Hz, 1H), 8.89 (t, J=1.6 Hz, 1H), 8.25 (dd, J=6.7 and 1.4 Hz, 1H), 7.49 (d, J=8.1 Hz, 2H), 7.20 (d, J=8.1 Hz, 2H), 2.38 (s, 3H), 1.27 (n-hexane grease peak), 0.91 (n-hexane grease peak). $^{13}$C NMR (150 MHz, CDCl$_3$): δ 152.0, 138.3, 136.9, 136.7, 129.3, 126.8, 125.0, 119.8, 29.7 (n-hexane grease peak). $^{125}$Te NMR (188 MHz, CDCl$_3$): δ 816.0. HRMS-FI: Calculated 271.9839, Found 271.9835, Δ=−1.38 ppm.

Examples 2L-2M: Preparation of
3-(4-methoxyphenyl)tellurophene (I-7)

The reaction was performed using 0.2 mmol of compound (II-15). Purification via column chromatography on silica gel (n-hexane) gave the chalcogenophene of formula (I-7) as a pale yellow solid. $^1$H NMR (600 MHz, CDCl$_3$): δ 8.90 (dd, J=6.7 and 1.9 Hz, 1H), 8.80 (t, J=1.7 Hz, 1H), 8.21 (dd, J=6.7 and 1.5 Hz, 1H), 7.51 (dt, J=9.7 and 2.5 Hz, 2H), 6.91 (dt, J=9.7 and 2.5 Hz, 2H), 3.82 (s, 3H). $^{13}$C NMR (150 MHz, CDCl$_3$): δ 158.7, 151.6, 138.3, 132.6, 128.0, 124.9, 118.8, 114.0, 55.3. $^{125}$Te NMR (188 MHz, CDCl$_3$): δ 813.6. HRMS-FI: Calculated 287.9788, Found 287.9785, Δ=−1.09 ppm.

Example 2N: Preparation of
3-(furan-2-yl)tellurophene (I-8)

The reaction was performed using 0.2 mmol of compound (II-17). Purification via column chromatography on silica gel (n-hexane) gave the chalcogenophene of formula (I-9) as a pale yellow solid. $^1$H NMR (600 MHz, CDCl$_3$): δ 8.99 (t, merged dd, J=1.6 Hz, 1H), 8.87 (dd, J=6.8 and 1.9 Hz, 1H), 8.18 (dd, J=6.8 and 1.4 Hz, 1H), 7.38-7.32 (m, 1H), 6.44 (dd, J=3.3 and 0.3 Hz, 1H), 6.40 (dd, J=3.3 and 1.7 Hz, 1H). $^{13}$C NMR (150 MHz, CDCl$_3$): δ 154.1, 142.0, 141.4, 136.0, 125.3, 118.0, 111.3, 104.8. HRMS-FI: Calculated 247.9475, Found 247.9480, Δ=1.82 ppm.

Example 2O: Preparation of
3-(thiophen-3-yl)tellurophene (I-9)

The reaction was performed using 0.2 mmol of compound (II-18). Purification via column chromatography on silica gel (n-hexane) gave the chalcogenophene of formula (I-10) as a pale yellow solid. $^1$H NMR (600 MHz, CDCl$_3$): δ 8.90-8.86 (m, 2H), 8.22 (dd, J=6.7 and 1.4 Hz, 1H), 7.36-7.30 (m, 3H). $^{13}$C NMR (150 MHz, CDCl$_3$): δ 146.7, 141.0, 137.9, 126.5, 125.8, 125.2, 120.3, 119.5. HRMS-FI: Calculated 263.9247, Found 263.9249, Δ=0.71 ppm.

Example 2P: Preparation of
3-(naphthalen-2-yl)tellurophene (I-10)

The reaction was performed using 0.2 mmol of compound (II-18). Purification via column chromatography on silica gel (n-hexane) gave the chalcogenophene of formula (I-8) as a yellow solid. $^1$H NMR (600 MHz, CDCl3): δ 9.06 (t, merged dd, J=1.7 Hz, 1H), 8.99-8.97 (m, unresolved dd, 1H), 8.40 (dd, J=6.7 and 1.4 Hz, 1H), 8.03 (d, J=1.2 Hz, 1H), 7.86-7.82 (m, 3H), 7.74 (dd, J=8.5 and 1.9 Hz, 1H), 7.50-7.45 (m, 2H). $^{13}$C NMR (150 MHz, CDCl3): δ 152.0, 138.3, 136.9, 133.6, 132.4, 128.2, 128.1, 127.6, 126.3, 125.8, 125.5, 125.4, 125.3, 121.1. HRMS-FI: Calculated 307.9839, Found 307.9843, Δ=1.27 ppm.

The results of Examples 2A-2P indicate that the first protocol P1 is suitable for a variety of substitution pattern on the starting compound of formula (II). Both alkyl (Examples 2A-2F) and aryl (Examples 2G-2P) substituents were successfully introduced in the 3 position of the produced chalcogenophenes. Under the conditions reported for the first protocol P1, desilylation was usually observed, resulting in a 3-functionalized chalcogen rather than a 2,4-functionalized chalcogen. As shown by the Examples 2K and 2M, increasing the reaction time might result in an increase of about 10% in the isolated yield of chalcogenophene compound.

Comparative Examples 1-4

Comparative Examples 1-4 were run according to the first protocol FP1, excluding either or both of the additive and the base, changing the amount of chalcogen used, or varying the temperature of the reaction, as indicated in Table 4 below. In all four cases, no chalcogenophene compound (I) could be isolated.

TABLE 4

Conditions for Comparative Examples 1-4

| Entry (Compound) | Reactant of formula (II) | Chalcogen (equiv.[a]) | Additive (v/v[b]) | Base | Temp. (° C.) | Time (h) |
|---|---|---|---|---|---|---|
| Comparative Example 1 | II-1 | Te (2.5) | —[c] | —[c] | 75 | 3 |
| Comparative Example 2 | II-1 | Te (2.5) | —[c] | KOH | 75 | 3 |
| Comparative Example 3 | II-1 | Te (3.0) | H$_2$O (8:2) | —[c] | 75 | 3 |
| Comparative Example 4 | II-1 | Te (3.0) | H$_2$O (8:2) | KOH | 25 | 3 |

[a]equiv. added for 1 mol. of reactant (II)
[b]volume of solvent/volume of additive
[c]Not added Comparison of the results of Table 4 and Table 3 suggests the importance with certain solvents (ethanol, in the examples above) of including both an additive (H$_2$O) and a base for the reaction to proceed. As indicated by Comparative Example 4 and Example 3, increasing the temperature might effectively promote the reaction for less activated substrates (for example, when producing alkyl functionalized chalcogenophenes).

In the Comparative Examples 1-4 and in the Examples 2A-2E, other products beside the chalcogenophene compound (I-1) were isolated, namely a compound of formula (II-23) and a compound of formula (V-1), in the amount indicated in Table 5.

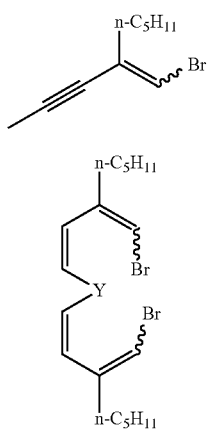

(II-23)

(V-1)

TABLE 5

Products distribution for Examples 2A-2E and Comparative Examples 1-4

| Entry | (I-1) Yield[a] (%) | (II-23) Yield[a] (%) | (V-1) Yield[a] (%) |
|---|---|---|---|
| Example 2A | 32 | 27 | 26 |
| Example 2B | 63 | Not isolated | 27 |
| Example 2C | 76 | Not isolated | 18 |
| Example 2D | 62 | Not isolated | 32 |
| Example 2E | 69 | Not isolated | 19 |
| Comparative Example 1 | Not isolated | 84 | Not isolated |
| Comparative Example 2 | Not isolated | 85 | Not isolated |
| Comparative Example 3 | Not isolated | 77 | Not isolated |
| Comparative Example 4 | Not isolated | 82 | Not isolated |

[a]Isolated yield

Without being bound to or limited by any chemical theory, formation of the compound of formula (II-23) may be explained by desilylation and debromination (not necessarily in this order) of the starting material (II-1). The compound of formula (II-23) is likely to be an intermediate towards the chalcogenophene compound (I-1), possibly through a chalcogenol species according to formula (IV) as discussed above.

It can be envisioned that the chalcogenol (IV) may either cyclize or attack a second compound of formula (II) to yield compounds of formula (V), of which compound (V-1) is an example.

Examples 3A-3H: Preparation of Functionalized Chalcogenophenes with Addition of Base <Second Protocol P2 for the Preparation of Functionalized Chalcogenophenes>

Elemental chalcogen (2.1 mmol, 2.1 equiv) was suspended in a liquid system (10 mL) constituted by the degassed N,N-dimethylformamide and tert-butanol. The ratio between the volume of N,N-dimethylformamide and the volume of tert-butanol used was of 99:1. The elemental chalcogen was treated with sodium borohydride (4.5 mmol, 4.5 equiv.) under nitrogen in a 2-neck round bottom flask fitted with a condenser. The mixture was heated to a temperature in the range from 80° C. to 100° C. for a time in the range from 0.5 hours to 1.0 hour. The solution was subsequently cooled to 0° C. or ambient temperature and a degassed solution of a compound of formula (II) (1.0 mmol, 1.0 equiv) in N,N-dimethylformamide (4.0 mL) was slowly added. After allowing the system to reach ambient temperature, grounded KOH (2.0 mmol, 2.0 equiv) was added directly. The reactions were stirred for the times and at the temperatures indicated in Table 6. The reactions were quenched by stirring vigorously while exposed to laboratory air, diluted with ethyl acetate (50 mL) and filtered through celite. The filtrate was washed twice with water (50 mL each) and once with brine (50 mL) and was dried over magnesium sulfate. After evaporation of the solvent, the residue was purified by silica gel chromatography (eluent system indicated in the characterization data of each compound) to afford functionalized chalcogenophene compounds (I) in the yields reported in Table 6.

TABLE 6

Preparation of chalcogenophene compounds according to the second protocol P2

| Entry | Product of formula (I) | Reactant of formula (II) | Chalcogen | Temp. (° C.) | Time (h) | Yield[a] (%) |
|---|---|---|---|---|---|---|
| Example 3A | I-1 | II-1 | Te | 75 | 2 | 32 |
| Example 3B | I-1 | II-1 | Te | 140 | 2 | 78 |

TABLE 6-continued

Preparation of chalcogenophene compounds according to the second protocol P2

| Entry | Product of formula (I) | Reactant of formula (II) | Chalcogen | Temp. (° C.) | Time (h) | Yield[a] (%) |
|---|---|---|---|---|---|---|
| Example 3C | I-11 | II-2 | Se | 140 | 3 | 54 |
| Example 3D | I-12 | II-3 | Te | 140 | 3 | 82 |
| Example 3E | I-3 | II-4 | Te | 140 | 0.5 | 97 |
| Example 3F | I-13 | II-7 | Te | 25 | 0.5 | 52 |
| Example 3G | I-13 | II-7 | Te | 25 | 20 | 87 |
| Example 3H | I-13 | II-7 | Te | 140 | 0.5 | 91 |
| Comparative Example 5 | —[b] | II-1 | Te | 25 | 2 | —[b] |

[a]Isolated yield
[b]Not isolated

Example 3C: Preparation of 3-n-heptylselenophene (I-11)

The reaction was performed using 0.2 mmol of compound (II-2). Purification via column chromatography on silica gel (n-hexane) afforded the chalcogenophene (I-11) as a brown liquid. $^1$H NMR (600 MHz, CDCl$_3$): δ 7.89 (dd, J=5.4 and 2.5 Hz, 1H), 7.52-7.51 (m, 1H), 7.20 (dd, J=5.4 and 1.2 Hz, 1H), 2.59 (t, J=7.7 Hz, 2H), 1.63-1.58 (m, 2H), 1.31-1.25 (m, 8H), 0.87 (t, J=7.0 Hz, 3H). $^{13}$C NMR (150 MHz, CDCl$_3$): δ 145.3, 131.4, 129.6, 123.7, 31.9, 31.8, 30.4, 29.3, 29.1, 22.6, 14.1. HRMS-FI: Calculated 230.0568, Found 230.0573, Δ=2.41 ppm.

Example 3D: Preparation of 4-n-heptyl-2-phenyltellurophene (I-12)

The reaction was performed using 0.2 mmol of compound (II-3). Purification via column chromatography on silica gel (n-hexane) afforded the chalcogenophene (I-12) as a light brown liquid. $^1$H NMR (600 MHz, CDCl$_3$): δ 8.20 (d, J=1.1 Hz, 1H), 7.76 (d, J=1.6 Hz, 1H), 7.46-7.44 (m, 2H), 7.33-7.30 (m, 2H), 7.27-7.24 (m, 1H), 2.58 (t, J=7.7 Hz, 2H), 1.66-1.60 (m, 2H), 1.34-1.25 (m, 8H), 0.88 (t, J=7.0 Hz, 3H). $^{13}$C NMR (100 MHz, CDCl$_3$): δ 153.7, 147.3, 140.1, 135.4, 128.8, 127.4, 126.8, 117.2, 35.4, 31.8, 30.2, 29.3, 29.1, 22.7, 14.1. $^{125}$Te NMR (188 MHz, CDCl$_3$): δ 753.5. HRMS-FI: Calculated 356.0778, Found 356.0772, Δ=−1.64 ppm.

Examples 3F-3H: Preparation of 2-(tert-butyl)-4-phenyltellurophene (I-13)

The reaction was performed using 0.2 mmol of compound (II-7). Purification via column chromatography on silica gel (n-hexane) afforded the chalcogenophene (I-13) as a light brown liquid. $^1$H NMR (400 MHz, CDCl$_3$): δ 8.66 (d, J=1.6 Hz, 1H), 7.76 (d, J=1.6 Hz, 1H), 7.56-7.53 (m, 2H), 7.38-7.33 (m, 2H), 7.28-7.24 (m, 1H), 1.4 (s, 9H). $^{13}$C NMR (100 MHz, CDCl$_3$): δ 166.1 151.5, 140.3, 131.6, 128.5, 126.8 (2 peaks merged), 116.8, 38.8, 34.0. HRMS-FI: Calculated 314.0309, Found 314.0305, Δ=−1.2 ppm.

Comparative Example 5

Comparative Example 5 was run according to the second protocol P2, stirring the reaction at the indicated temperature for the indicated amount of time. No chalcogenophene compound could be isolated.

Examples 3A, 3B, and 3D, and Comparative Example 5, show how less active substrates (for example, alkyl substituted compounds of formula (II)) can successfully react by increasing the temperature. Example 3E indicates that even for reactive substrate (for example, aryl substituted compounds of formula (II)), an increase of the reaction temperature can significantly shorten the reaction time (all the way down to 0.5 hours) without affecting the isolated yield of chalcogenophene (I). Example 3C indicates that the reaction is successful also for selenophene compounds. Examples 3F-3H indicate that the reaction tolerates well sterically hindered groups. In the Examples 3A-3H, no product according to formula (V) was observed, indicating that solvents which better dissolve compounds of formula (II) or formula (III) might help the reaction to proceed towards chalcogenophene compounds of formula (I).

Examples 4A-4T: Preparation of Chalcogenophene Compounds

<Third Protocol P3 for the Preparation of Functionalized Chalcogenophenes>

Elemental chalcogen (2.1 mmol, 2.1 equiv) was suspended in a liquid system (10 mL) constituted by degassed N,N-dimethylformamide with added tert-butanol. The ratio between the volume of N,N-dimethylformamide and the volume of tert-butanol used was of 99:1. The elemental chalcogen was treated with sodium borohydride (4.5 mmol, 4.5 equiv) under nitrogen in a 2-neck round bottom flask fitted with a condenser. The mixture was heated to a temperature in the range from 80° C. to 100° C. for a time in the range from 0.5 hours to 1.0 hour. The solution was subsequently cooled to 0° C. or ambient temperature and a degassed solution of a compound of formula (II) (1.0 mmol, 1.0 equiv) in N,N-dimethylformamide (4.0 mL) was slowly added. Each reaction was stirred for the time and at the temperature indicated in Table 7. Each reaction was quenched by stirring vigorously while exposed to laboratory air, diluted with ethyl acetate (50 mL) and filtered through celite. The filtrate was washed twice with water (50 mL each) and once with brine (50 mL) and was dried over magnesium sulfate. After evaporation of the solvent, the residue was purified by silica gel chromatography (eluent system indicated in the characterization data of each compound) to afford a functionalized chalcogenophene compound in the yield reported in Table 7.

TABLE 7

Preparation of chalcogenophene compound according to the third protocol P3

| Entry | Product of formula (I) | Reactant of formula (II) | Chalcogen | Temp. (° C.) | Time (h) | Yield[a] (%) |
|---|---|---|---|---|---|---|
| Example 4A | I-1 | II-1 | Te | 140 | 6 | 41 |
| Example 4B | I-14 | II-4 | Te | 25 | 2 | 47 |
| Example 4C | I-15 | II-5 | Te | 25 | 1 | 98 |
| Example 4D | 1-3 | II-6 | Te | 25 | 24 | 84 |
| Example 4E | I-17 | II-7 | Te | 25 | 2 | 31 |
| Example 4F | I-17 | II-7 | Te | 25 | 48 | 81 |
| Example 4G | I-18 | II-7 | Se | 25 | 12 | 64 |
| Example 4H | I-19 | II-8 | Te | 25 | 1 | 93 |
| Example 4I | I-20 | II-10 | Te | 25 | 1 | 92 |
| Example 4J | I-21 | II-11 | Se | 25 | 12 | 68 |
| Example 4K | I-22 | II-11 | Se | 25 | 1 | 71 |
| Example 4L | I-23 | II-12 | Te | 25 | 1 | 91 |
| Example 4M | I-24 | II-14 | Te | 25 | 1 | 91 |

TABLE 7-continued

Preparation of chalcogenophene compound according to the third protocol P3

| Entry | Product of formula (I) | Reactant of formula (II) | Chalcogen | Temp. (° C.) | Time (h) | Yield[a] (%) |
|---|---|---|---|---|---|---|
| Example 4N | I-25 | II-14 | Se | 25 | 1 | 67 |
| Example 4O | I-26 | II-15 | Te | 25 | 2 | 39 |
| Example 4P | I-27 | II-16 | Te | 25 | 1 | 89 |
| Example 4Q | I-28 | II-19 | Te | 25 | 1 | 96 |
| Example 4R | I-29 | II-20 | Te | 25 | 2 | 42 |
| Example 4S | I-30 | II-21 | Te | 25 | 1 | 94 |
| Example 4T | I-31 | II-22 | Te | 25 | 24 | 82 |
| Comparative Example 6 | — | II-1 | Te | 25 | 20 | — |

[a]Isolated yield

Example 4B: Preparation of 4-phenyl-2-(trimethylsilyl)tellurophene (I-14)

The reaction was performed using 0.2 mmol of compound (II-4). Purification via column chromatography on silica gel (n-hexane) afforded the chalcogenophene (I-14) as a pale yellow liquid. $^1$H NMR (400 MHz, CDCl$_3$): δ 9.18 (d, J=1.5 Hz, 1H), 8.48 (d, J=1.5 Hz, 1H), 7.59-7.56 (m, 2H), 7.40-7.35 (m, 2H), 7.31-7.26 (m, 1H), 0.32 (s, 9H). $^{13}$C NMR (100 MHz, CDCl$_3$): δ 154.9, 147.0, 144.0, 140.0, 128.6, 127.1, 127.0, 125.2, 0.8. HRMS-FI: Calculated 330.0078, Found 330.0073, Δ=−1.63 ppm.

Example 4C: Preparation of 2,4-diphenyltellurophene (I-15)

The reaction was performed using 0.2 mmol of compound (II-5). Purification via column chromatography on silica gel (n-hexane) afforded the chalcogenophene (I-15) as a pale yellow solid. $^1$H NMR (600 MHz, CDCl$_3$): δ 8.79 (d, J=1.4 Hz, 1H), 8.25 (d, J=1.4 Hz, 1H), 7.61 (t, J=4.1 Hz, 2H), 7.52 (t, J=4.1 Hz, 2H), 7.40 (t, J=7.7 Hz, 2H), 7.35 (t, J=7.7 Hz, 2H), 7.32-7.28 (m, 2H). $^{13}$C NMR (150 MHz, CDCl$_3$): (152.7, 148.4, 139.9 (2 peaks merged), 133.6, 128.9, 128.6, 127.7, 127.1, 126.9, 126.8, 119.8. $^{125}$Te NMR (188 MHz, CDCl$_3$): δ 805.9. HRMS-FI: Calculated 333.9996, Found 333.9995, Δ=−0.13 ppm.

Example 4D: Preparation of 3-phenyltellurophene (I-3)

The reaction was performed using 0.2 mmol of compound (II-6). Purification via column chromatography on silica gel (n-hexane) afforded the chalcogenophene (I-15) as a pale yellow solid.

Examples 4E-4F: Preparation of 2-(tert-butyl)-4-phenyltellurophene (I-17)

The reaction was performed on 0.2 mmol of compound (II-7). Purification via column chromatography on silica gel (n-hexane) afforded the chalcogenophene (I-17) as a light brown liquid. $^1$H NMR (400 MHz, CDCl$_3$): δ 8.66 (d, J=1.6 Hz, 1H), 7.76 (d, J=1.6 Hz, 1H), 7.56-7.53 (m, 2H), 7.38-7.33 (m, 2H), 7.28-7.24 (m, 1H), 1.4 (s, 9H). $^{13}$C NMR (100 MHz, CDCl$_3$): (166.1 151.5, 140.3, 131.6, 128.5, 126.8 (2 peaks merged), 116.8, 38.8, 34.0. HRMS-FI: Calculated 314.0309, Found 314.0305, Δ=−1.2 ppm.

Example 4G: Preparation of 2-(tert-Butyl)-4-phenylselenophene (I-18)

The reaction was performed on 0.2 mmol of compound (II-7). Purification via column chromatography on silica gel (n-hexane) afforded the chalcogenophene (I-18) as a light brown liquid. $^1$H NMR (400 MHz, CDCl$_3$): δ 7.86 (d, J=1.5 Hz, 1H), 7.57-7.54 (m, 2H), 7.38-7.34 (m, 2H), 7.31 (d, J=1.5 Hz, 1H), 7.28-7.24 (m, 1H), 1.43 (s, 9H). $^{13}$C NMR (100 MHz, CDCl$_3$): δ 166.0, 143.9, 137.8, 128.6, 126.8, 126.5, 123.5, 122.2, 36.6, 33.1. HRMS-FI: Calculated 264.0411, Found 264.0408, Δ=−1.22 ppm.

Example 4H: Preparation of 4-phenyl-2-(p-tolyl)tellurophene (I-19)

The reaction was performed on 0.2 mmol of compound (II-8). Purification via column chromatography on silica gel (n-hexane) afforded the chalcogenophene (I-19) as a pale yellow solid. $^1$H NMR (400 MHz, CDCl$_3$): δ 8.74 (d, J=1.5 Hz, 1H), 8.19 (d, J=1.5 Hz, 1H), 7.60 (d, J=7.2 Hz, 2H), 7.41-7.37 (m, 4H), 7.31-7.28 (m, 1H), 7.15 (d, J=8 Hz, 2H), 2.34 (s, 3H), 1.23 (n-hexane grease peak), 0.86 (n-hexane grease peak). $^{13}$C NMR (100 MHz, CDCl$_3$): δ 152.7, 148.5, 140.0, 137.7, 137.2, 133.0, 129.6, 128.6, 127.1, 126.8, 126.7, 119.1, 29.7 (n-hexane grease peak), 21.1. HRMS-FI: Calculated 348.0152, Found 348.0149, Δ=−0.69 ppm.

Example 4I: Preparation of 4-(4-chlorophenyl)-2-phenyltellurophene (I-20)

The reaction was performed on 0.2 mmol of compound (II-10). Purification via column chromatography on silica gel (n-hexane) afforded the chalcogenophene (I-20) as an off-white solid. $^1$H NMR (400 MHz, CDCl$_3$): δ 8.78 (d, J=1.6 Hz, 1H), 8.18 (d, J=1.6 Hz, 1H), 7.54-7.48 (m, 4H), 7.37-7.32 (m, 4H), 7.31-7.27 (m, 1H). $^{13}$C NMR (100 MHz, CDCl$_3$): δ 151.3, 148.9, 139.8, 138.3, 133.1, 132.9, 129.0, 128.8, 128.0, 127.9, 126.9, 120.3. HRMS-FI: Calculated 367.9606, Found 367.9594, Δ=−3.39 ppm.

Example 4J: Preparation of 4-(4-(trifluoromethyl)phenyl)selenophene (I-21)

The reaction was performed on 0.2 mmol of compound (II-11). Purification via column chromatography on silica gel (n-hexane) afforded the chalcogenophene (I-21) as a yellow solid. $^1$H NMR (600 MHz, CDCl$_3$): δ 8.19 (dd, J=2.5 and 1.4 Hz, 1H), 8.09 (dd, J=5.5 and 2.5 Hz, 1H), 7.68-7.66 (m, 3H), 7.63 (d, J=8.3 Hz, 2H), 1.25 (n-hexane grease peak), 0.87 (n-hexane grease peak). $^{13}$C NMR (150 MHz, CDCl$_3$): δ 143.2, 140.5, 131.5, 129.2, 129.0 (q, J=32.4 Hz), 127.1, 126.8, 125.7 (q, J=3.6 Hz), 124.3 (q, J=270.9 Hz), 29.7 (n-hexane grease peak). $^{19}$F NMR (563 MHz, CDCl$_3$): δ −62.2 (s, CF$_3$). $^{77}$Se NMR (598 MHz, CDCl$_3$): δ 627.4. HRMS-FI: Calculated 275.9660, Found 275.9662, Δ=1.07 ppm.

Example 4K: Preparation of 4-(4-(trifluoromethyl)phenyl)-2-(trimethylsilyl)selenophene (I-22)

The reaction was performed using 0.2 mmol of compound (II-11). Purification via column chromatography on silica gel (n-hexane) afforded the chalcogenophene (I-22) as an off white solid. $^1$H NMR (600 MHz, CDCl$_3$): δ 8.44 (d, J=1.0 Hz, 1H), 7.83 (d, J=1.0 Hz, 1H), 7.70 (d, J=8.2 Hz, 2H), 7.64 (d, J=8.2 Hz, 2H), 0.38 (s, 9H). $^{13}$C NMR (150 MHz, CDCl$_3$): δ 150.1, 144.8, 140.6, 135.8, 132.2, 128.9 (q, J=32.4 Hz), 127.0, 125.7 (q, J=3.6 Hz), 124.3 (q, J=271.3 Hz), 0.25. $^{19}$F NMR (563 MHz, CDCl$_3$): δ −62.3 (s, CF$_3$). $^{77}$Se NMR (598 MHz, CDCl$_3$): δ 688.0. HRMS-FI: Calculated 348.0054, Found 348.0045, Δ=−2.71 ppm.

Example 4L: Preparation of 2-phenyl-4-(4-(trifluoromethyl)phenyl)tellurophene (I-23)

The reaction was performed using 0.2 mmol of compound (II-12). Purification via column chromatography on silica gel (n-hexane) afforded the chalcogenophene (I-23) as an off white solid. $^1$H NMR (600 MHz CDCl$_3$): δ 8.89 (d, J=1.6 Hz, 1H), 8.24 (d, J=1.6 Hz, 1H), 7.69 (d, J=8.5 Hz, 2H), 7.65 (d, J=8.5 Hz, 2H), 7.52-7.50 (m, 2H), 7.38-7.35 (m, 2H), 7.33-7.30 (m, 1H). $^{13}$C NMR (150 MHz, CDCl$_3$): δ 151.2, 149.4, 143.1, 139.6, 132.9, 129.0, 128.9 (q, J=32.4), 128.0, 127.0, 126.9, 125.6 (q, J=3.9 Hz), 124.3 (q, J=271.0 Hz), 121.9. $^{19}$F NMR (563 MHz, CDCl$_3$): δ −62.3 (s, CF$_3$). HRMS-FI: Calculated 401.9869, Found 401.9865, Δ=−1.05 ppm.

Example 4M: Preparation of 2-phenyl-4-(p-tolyl)tellurophene (I-24)

The reaction was performed using 0.2 mmol of compound (II-14). Purification via column chromatography on silica gel (n-hexane) afforded the chalcogenophene (I-24) as a pale yellow solid. $^1$H NMR (400 MHz, CDCl$_3$): δ 8.73 (d, J=1.6 Hz, 1H), 8.22 (d, J=1.6 Hz, 1H), 7.51-7.48 (m, 4H), 7.36-7.32 (m, 2H), 7.30-7.26 (m, 1H), 7.19 (d, J=7.9 Hz, 2H), 2.36 (s, 3H). $^{13}$C NMR (100 MHz, CDCl$_3$): δ 152.6, 148.1, 140.0, 137.2, 136.9, 133.7, 129.3, 128.9, 127.7, 126.9, 126.7, 118.9, 21.2. HRMS-FI: Calculated 348.0152, Found 348.0150, Δ=−0.55 ppm.

Example 4N: Preparation of 2-phenyl-4-(p-tolyl)selenophene (I-25)

The reaction was performed using 0.2 mmol of compound (II-14). Purification via column chromatography on silica gel (n-hexane) afforded the chalcogenophene (I-25) as an off-white solid. $^1$H NMR (400 MHz, CDCl$_3$): δ 7.94 (d, J=1.4 Hz, 1H), 7.77 (d, J=1.4 Hz, 1H), 7.60-7.57 (m, 2H), 7.51-7.48 (m, 2H), 7.39-7.35 (m, 2H), 7.31-7.27 (m, 1H), 7.20 (d, J=8.0 Hz, 2H), 2.36 (s, 3H). $^{13}$C NMR (100 MHz, CDCl$_3$): δ 150.6, 145.4, 136.9, 136.4, 134.6, 129.5, 128.9, 127.7, 126.4, 126.3, 125.3, 124.0, 21.2. HRMS-FI: Calculated 298.0255, Found 298.0247, Δ=−2.55 ppm.

Example 4O: Preparation of 4-(4-methoxyphenyl)-2-(trimethylsilyl)tellurophene (I-26)

The reaction was performed using 0.2 mmol of compound (II-15). Purification via column chromatography on silica gel (n-hexane) afforded the chalcogenophene (I-26) as an off-white solid. $^1$H NMR (400 MHz, CDCl$_3$): δ 9.06 (d, J=1.4 Hz, 1H), 8.45 (d, J=1.4 Hz, 1H), 7.53-7.50 (m, 2H), 6.93-6.90 (m, 2H), 3.82 (s, 3H), 0.31 (s, 9H). $^{13}$C NMR (100 MHz, CDCl$_3$): δ 158.7, 154.3, 146.5, 144.1, 132.9, 128.2, 123.3, 114.0, 55.3, 0.8. HRMS-FI: Calculated 360.0184, Found 360.0189, Δ=1.49 ppm.

Example 4P: Preparation of 4-(4-methoxyphenyl)-2-phenyltellurophene (21-27)

The reaction was performed using 0.2 mmol of compound (II-16). Purification via column chromatography on silica gel (n-hexane) afforded the chalcogenophene (I-27) as a pale yellow solid. $^1$H NMR (400 MHz, CDCl$_3$): δ 8.65 (d, J=1.5 Hz, 1H), 8.20 (d, J=1.5 Hz, 1H), 7.55-7.49 (m, 4H), 7.36-7.26 (m, 3H), 6.92 (dt, J=8.7 and 2.4 Hz, 2H), 3.83 (s, 3H). $^{13}$C NMR (100 MHz, CDCl$_3$): δ 158.8, 152.1, 148.0, 140.0, 133.6, 132.8, 128.9, 127.9, 127.7, 126.8, 118.0, 114.0, 55.3. HRMS-FI: Calculated 364.0101, Found 364.0102, Δ=0.28 ppm.

Example 4Q: Preparation of 4-(4-bromophenyl)-2-phenyltellurophene (I-28)

The reaction was performed using 0.2 mmol of compound (II-19). Purification via column chromatography on silica gel (n-hexane) afforded the chalcogenophene (I-28) as an off-white solid. $^1$H NMR (400 MHz, CDCl$_3$): δ 8.78 (d, J=1.6 Hz, 1H), 8.18 (d, J=1.6 Hz, 1H), 7.52-7.44 (m, 6H), 7.37-7.27 (m, 3H). $^{13}$C NMR (100 MHz, CDCl$_3$): δ 151.4, 149.0, 139.7, 138.8, 133.1, 131.7, 129.0, 128.4, 127.9, 126.9, 121.1, 120.4. HRMS-FI: Calculated 411.9083, Found 411.9075, Δ=−6.15 ppm.

Example 4R: Preparation of 4-(naphthalen-2-yl)-2-(trimethylsilyl)tellurophene (I-29)

The reaction was performed using 0.2 mmol of compound (II-20). Purification via column chromatography on silica gel (n-hexane) afforded the chalcogenophene (I-29) as an off-white solid. $^1$H NMR (600 MHz, CDCl$_3$): δ 9.31 (d, J=1.3 Hz, 1H), 8.62 (d, J=1.3 Hz, 1H), 8.02 (s, 1H), 7.86-7.81 (m, 3H), 7.73 (dd, J=8.5 and 1.7 Hz, 1H), 7.49-7.44 (m, 2H), 0.35 (s, 9H). $^{13}$C NMR (150 MHz, CDCl$_3$): δ 154.7, 147.1, 144.0, 137.2, 133.6, 132.4, 128.2, 128.1, 127.6, 126.2, 125.8 (2 peaks merged), 125.7, 125.5, 0.9. HRMS-FI: Calculated 380.0234, Found 380.0237, Δ=0.63 ppm.

Example 4S: Preparation of 4-(Naphthalen-2-yl)-2-phenyltellurophene (I-30)

The reaction was performed using 0.2 mmol of compound (II-21). Purification via column chromatography on silica gel (n-hexane) afforded the chalcogenophene (I-30) as a pale yellow solid. $^1$H NMR (600 MHz, CDCl$_3$): δ 8.92 (d, J=1.4 Hz, 1H), 8.38 (d, J=1.4 Hz, 1H), 8.04 (s, 1H), 7.86 (d, J=8.5 Hz, 2H), 7.83 (d, J=7.7 Hz, 1H), 7.75 (dd, J=8.5 and 1.6 Hz, 1H), 7.55 (d, J=7.6 Hz, 2H), 7.49-7.44 (m, 2H), 7.36 (t, J=7.6 Hz, 2H), 7.30 (t, J=7.3 Hz, 1H). $^{13}$C NMR (150 MHz, CDCl$_3$): δ 152.6, 148.5, 140.0, 137.2, 133.7, 133.6, 132.5, 129.0 (2 peaks merged), 128.3, 128.1, 127.8, 127.6, 126.9, 126.3, 125.8, 125.3, 120.2. HRMS-FI: Calculated 384.0152, Found 384.0159, Δ=1.98 ppm.

Example 4T: Preparation of 3-(naphthalen-2-yl)tellurophene (I-31)

The reaction was performed using 0.2 mmol of compound (II-21). Purification via column chromatography on silica gel (n-hexane) afforded the chalcogenophene (I-30) as a yellow solid. $^1$H NMR (600 MHz, CDCl$_3$): δ 9.06 (t, merged dd, J=1.7 Hz, 1H), 8.99-8.97 (m, unresolved dd, 1H), 8.40 (dd, J=6.7 and 1.4 Hz, 1H), 8.03 (d, J=1.2 Hz, 1H), 7.86-7.82 (m, 3H), 7.74 (dd, J=8.5 and 1.9 Hz, 1H), 7.50-7.45 (m, 2H). $^{13}$C NMR (150 MHz, CDCl$_3$): δ 152.0, 138.3, 136.9, 133.6, 132.4, 128.2, 128.1, 127.6, 126.3, 125.8, 125.5, 125.4, 125.3, 121.1. HRMS-FI: Calculated 307.9839, Found 307.9843, Δ=1.27 ppm.

Comparative Example 6

Comparative Example 6 was run according to the second protocol P3, stirring the reaction at the indicated temperature for the indicated amount of time. No chalcogenophene compound could be observed.

The results in Table 7 show that it is possible to perform the reaction without addition of base and, at least in the case of aryl substituted starting material, at ambient temperature. Furthermore, the present invention provides a straightforward and convenient access route to 2,4-difunctionalized chalcogenophenes. Both tellurophenes and selenophenes have been successfully prepared. Example 4A indicates that even for less activated starting materials (for example, alkyl substituted compounds of formula (II)), the reaction can proceed in absence of base, by heating the system to higher temperatures. As indicated by Examples 4E and 4F, even in presence of sterically hindered substrates the reaction can proceed at standard ambient temperature with good yield, provided that enough time is given to the substrate to react. Furthermore, as shown at least by Examples 4B, 4K, 4O, and 4R, the milder reaction conditions of protocol P3 allows retention in the final product of labile groups such as the silyl group.

This invention has been disclosed above in the preferred embodiments, but is not limited to those. It is known to one skilled in the art that some modifications and innovations may be made without departing from the spirit and scope of this invention. Hence, the scope of this invention should be defined by the following claims.

What is claimed is:

1. A method of forming a chalcogenophene compound of formula (I), the method comprising reacting a compound of formula (II) with a chalcogenide salt in presence of a proton source,

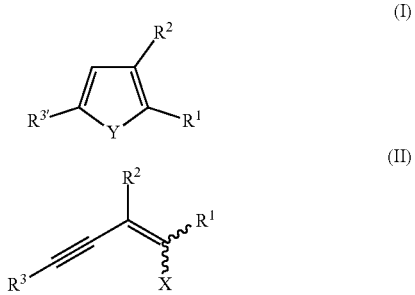

wherein, in formula (I) and in formula (II),
Y is O, S, Se, Te or Po,
$R^1$ is hydrogen, deuterium, a substituted or unsubstituted aliphatic, heteroaromatic, or aromatic group, or a precursor of a leaving group Z whose conjugate acid (HZ) has a $pK_a$ of less than 30,
$R^2$ is hydrogen, deuterium, or a substituted or unsubstituted aliphatic, heteroaromatic, or aromatic group,
$R^1$ and $R^2$ are the same or different, and may joint together to form a substituted or unsubstituted, saturated or unsaturated, heteroalicyclic or alicyclic ring,
$R^3$ is selected from the group consisting of hydrogen, substituted and unsubstituted alkyl, aryl, heteroaryl, alkanoyl, aryloyl, heteroaryloyl, organosilyl, organotin, and organogermyl groups,
$R^{3'}$ is the same as $R^3$ or is hydrogen; and
X is a precursor of a leaving group X whose conjugate acid (HX) has a $pK_a$ of less than 30.

2. The method of claim 1, wherein in the compound of formula (II) $R^1$ and X are independently one of a halogen atom, a mesylate group, a triflate group, a tosylate group, an alkanesulfonate group, or an arenesulfonate group.

3. The method of claim 2, wherein in formula (II) $R^1$ is the same as X.

4. The method of claim 1, wherein the compound of formula (II) is mixed with the chalcogenide salt.

5. The method of claim 1, wherein the reaction is carried in a solvent having a dielectric constant of at least 7.

6. The method of claim 5, wherein the reaction is stirred at standard ambient temperature.

7. The method of claim 6, wherein $R^2$ is a substituted or unsubstituted aromatic or heteroaromatic group.

8. The method of claim 5, further comprising adding an additive to the reaction, wherein the solvent is an aprotic solvent, and a $pK_a$ of the additive is less than 40.

9. The method of claim 8, wherein a volume ratio of the additive to the solvent is in a range from 0.001 to 5.

10. The method of claim 8, wherein the additive is a $C_1$ to $C_{12}$ alcohol.

11. The method of claim 5, wherein the solvent is the proton source.

12. The method of claim 5, wherein an additive having a dielectric constant higher than the dielectric constant of the solvent is added to the reaction, and a ratio of a volume of the solvent to a volume of the additive is in the range from 99:1 to 1:99.

13. The method of claim 12, wherein the solvent is a $C_1$ to $C_{12}$ alcohol, and the additive is water.

14. The method of claim 1, further comprising adding a base to the reaction, wherein a $pK_a$ of a conjugate acid of the base is less than 50.

15. The method of claim 14, wherein, when the dielectric constant of the solvent or the additive is less than 26, the base is selected from the group whose conjugate acid has a $pK_a$ in the range from 5 to 50.

16. The method of claim 15, wherein the base, its conjugated acid, or both are the proton source.

17. The method of claim 16, wherein an amphoteric compound is used as the base.

18. The method of claim 14, when the dielectric constant of the solvent or the additive is greater than 26, wherein the base is selected from the group consisting of an alcohol, a ketone, an ether, a nitrile, N,N-dimethylformamide, N,N-dimethylacetamide, dimethylsulfoxide, N-methyl-2-pyrrolidone, and hexamethylphosphoramide.

19. The method of claim 14, wherein $R^3$ is selected from the group consisting of substituted and unsubstituted organosilyl, organotin, and organogermyl groups.

20. The method of claim 1, further comprising heating a reaction system of the reaction at a temperature between 50° C. and 200° C.

* * * * *

UNITED STATES PATENT AND TRADEMARK OFFICE
CERTIFICATE OF CORRECTION

PATENT NO. : 10,407,402 B1  
APPLICATION NO. : 16/275278  
DATED : September 10, 2019  
INVENTOR(S) : Chien-Chung Han et al.

Page 1 of 1

It is certified that error appears in the above-identified patent and that said Letters Patent is hereby corrected as shown below:

In the Specification

At Column 2, Line 40-53 should read as follows:

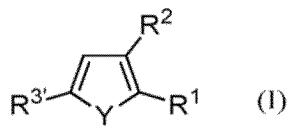   (I)

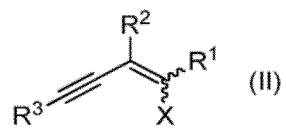   (II)

Signed and Sealed this  
Twelfth Day of November, 2019

Andrei Iancu  
*Director of the United States Patent and Trademark Office*